US009611238B2

(12) United States Patent
Serhan et al.

(10) Patent No.: US 9,611,238 B2
(45) Date of Patent: *Apr. 4, 2017

(54) 14-HYDROXY-DOCOSAHEXAENOIC ACID COMPOUNDS

(71) Applicant: The Brigham and Women's Hospital, Inc., Boston, MA (US)

(72) Inventors: Charles N. Serhan, Needham, MA (US); Rong Yang, Boston, MA (US)

(73) Assignee: The Brigham And Women's Hospital, Inc., Boston, MA (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/557,151

(22) Filed: Dec. 1, 2014

(65) Prior Publication Data

US 2015/0119463 A1    Apr. 30, 2015

Related U.S. Application Data

(63) Continuation of application No. 13/119,096, filed as application No. PCT/US2009/056998 on Sep. 15, 2009, now Pat. No. 8,927,747.

(60) Provisional application No. 61/138,652, filed on Dec. 18, 2008, provisional application No. 61/097,328, filed on Sep. 16, 2008.

(51) Int. Cl.
*A23K 20/158* (2016.01)
*A61K 31/202* (2006.01)
*A61K 8/365* (2006.01)
*A61K 8/37* (2006.01)
*A61K 8/49* (2006.01)
*A61Q 19/08* (2006.01)
*A61Q 5/00* (2006.01)
*C07C 59/42* (2006.01)
*C07C 69/732* (2006.01)
*C07D 303/12* (2006.01)
*C07D 303/38* (2006.01)

(52) U.S. Cl.
CPC .......... *C07D 303/38* (2013.01); *A23K 20/158* (2016.05); *A61K 8/365* (2013.01); *A61K 8/37* (2013.01); *A61K 8/4973* (2013.01); *A61K 31/202* (2013.01); *A61Q 5/006* (2013.01); *A61Q 19/08* (2013.01); *C07C 59/42* (2013.01); *C07C 69/732* (2013.01); *C07D 303/12* (2013.01); *Y02P 20/55* (2015.11)

(58) Field of Classification Search
CPC .... A23K 20/158; A23K 31/202; A23K 8/365; A23K 8/37; A23K 8/4973; A61Q 19/08; A61Q 5/006; C07C 59/42; C07C 69/732; C07D 303/12; C07D 303/38; Y02P 20/55
See application file for complete search history.

(56) References Cited

U.S. PATENT DOCUMENTS 8,927,747 B2 * 1/2015 Serhan .................... C07C 59/42
554/219
2006/0241088 A1   10/2006 Arterburn et al.

FOREIGN PATENT DOCUMENTS

| JP | 2003525880 A | 9/2003 |
| JP | 2005535712 A | 11/2005 |
| WO | WO 2006/055965 A2 | 5/2006 |
| WO | WO2006055965 | * 5/2006 |
| WO | WO 2007/127377 | 11/2007 |
| WO | WO 2008/070129 A2 | 6/2008 |

OTHER PUBLICATIONS

Office Action dated Jan. 16, 2015 for EP Application No. 09 815 065.9, 6 pgs.
Serhan, et al., "Maresins: novel macrophage mediators with potent anti-inflammatory and proresolving actions", Journal of Experimental Medicine, vol. 206, No. 1, Jan. 16, 2009, pp. 15-23, XP55041649.
Serhan, "Systems approach to inflammation resolution: identification of novel anti-inflammatory and pre-resolving mediators", Journal of Thrombosis and Haemostasis, vol. 7, Jul. 2009, pp. 44-48, XP55041646.
Arita, et al., "Stereochemical assignment, anti-inflammatory properties, and receptor for the omega-3 lipid mediator resolvin E1", *J. Exp. Med.*, No. 201, 2005, pp. 713-722.
Bannenberg, et al., "Molecular circuits of resolution: formation and actions of resolvins and protectins", *J. Immunol.* No. 174, 2005, pp. 4345-4355.
Calder, "Immunomodulation by omega-3 fatty acids. *Prostaglandins Leukot. Essent. Fatty Acids*", No. 77, 2007, pp. 327-335.
Cash, et al. "Synthetic chemerin-derived peptides suppress inflammation through ChemR23", *J. Exp. Med.* No. 205, 2008, pp. 767-775.
Colomer, et al., N-3 fatty acids, cancer and cachexia: a systematic review of the literature. *Br.J. Nutr.* No. 97, 2007, pp. 823-831.
Dwyer, et al., "Arachidonate 5-lipoxygenase promoter genotype, dietary arachidonic acid, and atherosclerosis", *N. Engl. J. Med.*, No. 350, 2004, pp. 29-37.
German, et al., "Lipoxygenase in trout gill tissue acting on arachidonic, eicosapentaenoic and docosahexaenoic acids", *Biochim. Biophys. Acta*, No. 875, 1986, pp. 12-20.
Gilroy, et al., "Inflammatory resolution: new opportunities for drug discovery", *Nat. Rev. Drug Discov.*, No. 3, 2004, pp. 401-416.
Godson, et al., "Cutting edge: Lipoxins rapidly stimulate nonphlogistic phagocytosis of apoptotic neutrophils by monocyte-derived macrophages", *J. Immunol.* No. 164, 2000, pp. 1663-1667.
Gronert, et al., "A role for the mouse 12/15-lipoxygenase pathway in promoting epithelial wound healing and host defense", *J. Biol. Chem.*, No. 280, 2005, pp. 15267-15278.
Hong, et al., "Novel docosatrienes and 17S-resolvins generated from docosahexaenoic acid in murine brain, human blood and glial cells: autacoids in anti-inflammation", *J. Biol. Chem.* No. 278, 2003, pp. 14677-14687.

(Continued)

*Primary Examiner* — Paul A Zucker
*Assistant Examiner* — Mark Luderer
(74) *Attorney, Agent, or Firm* — Christensen, Fonder, Dardi & Herbert PLLC; Colin L. Fairman

(57) ABSTRACT

The invention describes novel 14-hydroxy docosahexaenoic acid (DHA) analogues, their preparation, isolation, identification, purification and uses thereof.

15 Claims, 16 Drawing Sheets

(56) References Cited

OTHER PUBLICATIONS

Hudert, et al., "Transgenic mice rich in endogenous n-3 fatty acids are protected from colitis", *Proc. Natl. Acad. Sci. U.S.A.*, No. 103, 2006, pp. 11276-11281.

Kim, et al., "Stereochemical analysis of hydroxylated docosahexaenoates produced by human platelets and rat brain homogenate", *Prostaglandins*, No. 40, 1990 p. 473.

Maclean, et al., "Effects of omega-3 fatty acids on cancer risk: a systematic review", *JAMA*, No. 295, 2006, pp. 403-415.

Merched, et al., "Atherosclerosis: Evidence for impairment of resolution of vascular inflammation governed by specific lipid mediators", *FASEB J.*, No. 22, 2008, pp. 3595-3606.

Mukherjee, et al., "Neuroprotectin D1: a docosahexaenoic acid-derived docosatriene protects human retinal pigment epithelial cells from oxidative stress", *Proc. Natl. Acad. Sci. U.S.A.*, No. 101, 2004, pp. 8491-8496.

Nathan, "Points of control in inflammation", *Nature*, No. 420, 2002, pp. 846-852.

Rossi, et al., "Regulation of macrophage phagocytosis of apoptotic cells by cAMP", *J. Immunol*, No. 160, 1998, pp. 3562-3568.

Samuelsson, et al. "Leukotrienes: mediators of immediate hypersensitivity reactions and inflammation", *Science*, No. 220, 1983, pp. 568-575.

Schwab, et al., "Resolvin E1 and protectin D1 activate inflammation-resolution programmes", *Nature*, No. 447, 2007, pp. 869-874.

Serhan, et al., "Novel functional sets of lipid-derived mediators with antiinflammatory actions generated from omega-3 fatty acids via cyclooxygenase 2-nonsteroidal antiinflammatory drugs and transcellular processing". *J. Exp. Med.*, No. 192, 2000, pp. 1197-1204.

Serhan, et al., "Resolvins: a family of bioactive products of omega-3 fatty acid transformation circuits initiated by aspirin treatment that counter pro-inflammation signals", *J. Exp. Med.*, No. 196, 2002, pp. 1025-1037.

Extended European Search Report from related PCT Application PCT/US2009/056998, dated Nov. 7, 2012, 10 pages.

Office Action dated Jan. 31, 2014 for related Japanese Patent Application No. 2011-527902, 3 pages.

\* cited by examiner

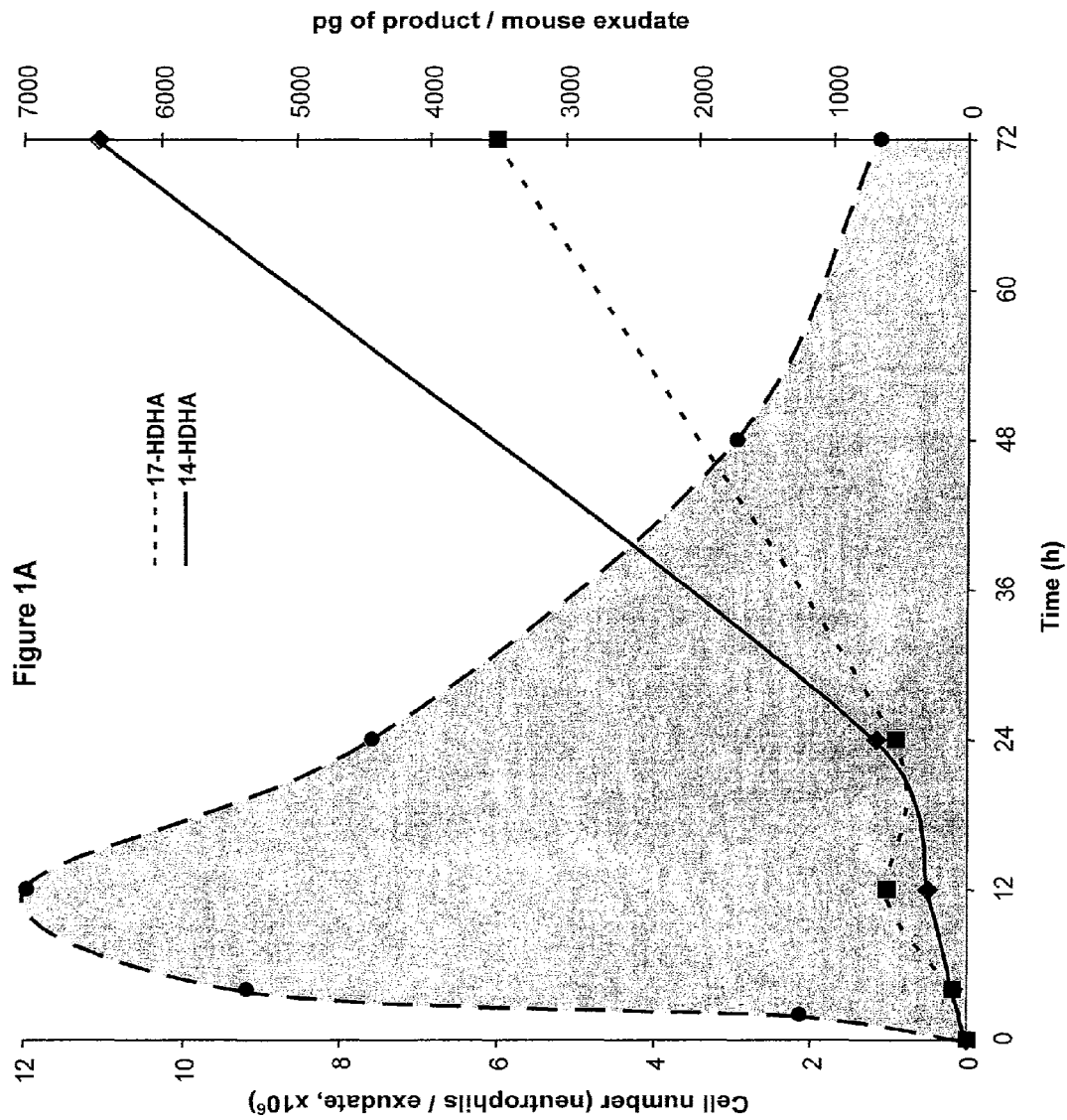

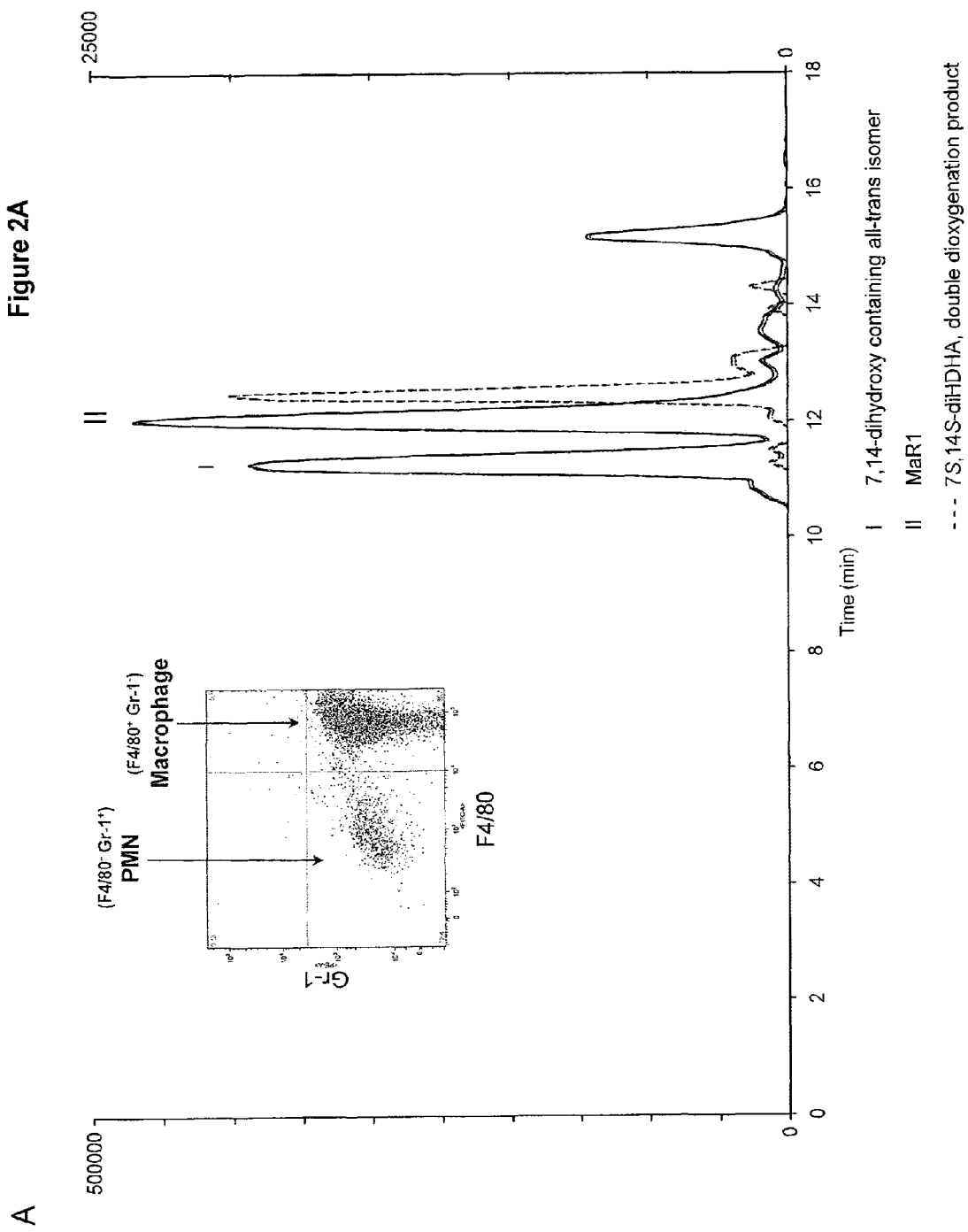

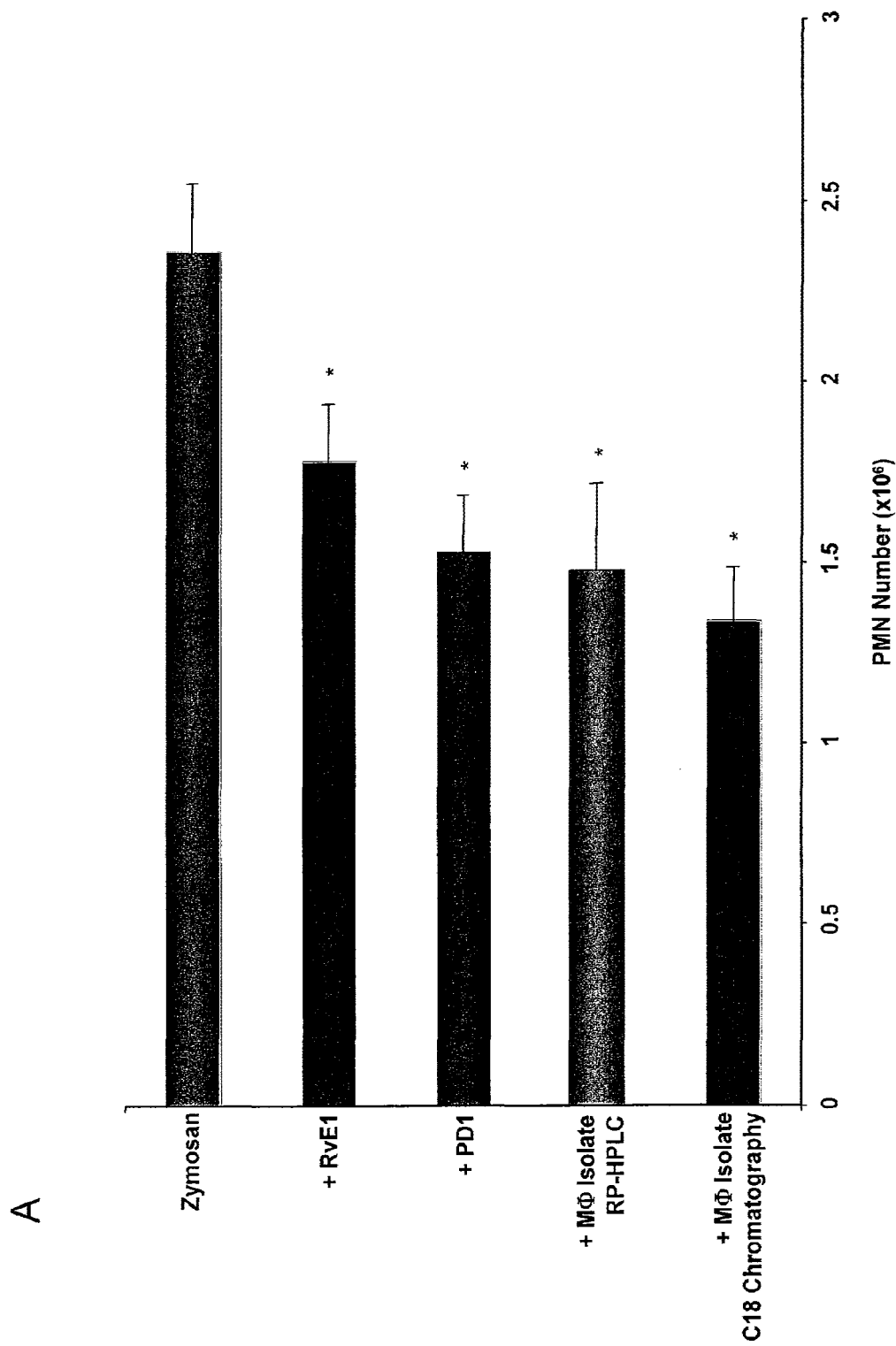

Methyl Maresin 1 analog preparation

22-trifluoro-maresin analog preparation

Figure 10. Structures, LC-MS and GC-MS fragmentation for novel 14-series compounds identified using mediator-based lipidomics.

| Compound | LC Retention Time (min) | LC-MS Major Fragment Ions[a] | GC-MS Major Fragment Ions[b] | C Value | UV $\lambda_{max}$[c] |
|---|---|---|---|---|---|
| 14S-HDHA | 17.1 | 343(M-H), 325, 299, 281, 233, 205, 189, 161 | 430(M), 321, 219, 211, 129, 121, 109 | 24.2 | 237 |
| MaR1 | 12.2 | 359(M-H), 341, 323, 315, 297, 279, 250, 221, 177, 161, 141, 123, 113 | 487(M-31), 428, 413, 409, 338, 307, 229, 217, 211, 139, 127, 121, 109 | 24.2, 26.0 | 270 |
| 7S,14S-dihydroxy (double dioxygenation product) | 12.6 | 359(M-H), 341, 323, 315, 297, 279, 250, 221, 177, 161, 141, 123, 113 | 409, 229, 217, 211, 139, 127, 121, 109 | 24.1 | 270 |
| 4,14-dihydroxy (minor) | 13.6 | 359(M-H), 341, 323, 315, 297, 279, 249, 221, 203, 177, 101 | 487(M-31), 428, 413, 409, 338, 307, 217, 211, 121, 109 | 24.2 | ~245 |
| 13,14-dihydroxy | - | - | 487(M-31), 428, 413, 409, 338, 313, 307, 223, 217, 211, 205, 121, 109 | 24.2, 25.0 | ~270 |

14-HYDROXY-DOCOSAHEXAENOIC ACID COMPOUNDS

CROSS REFERENCE TO RELATED APPLICATIONS

This application is a continuation of U.S. patent application Ser. No. 13/119,096, filed Jul. 29, 2011, which is a 371 of PCT/US09/56998, filed Sep. 15, 2009, which claims benefit under 35 U.S.C. §119(e) to U.S. Provisional Patent Application Ser. No. 61/138,652, entitled "14-HYDROXY-DOCOSAHEXAENOIC ACID COMPOUNDS", filed Dec. 18, 2008, and U.S. Provisional Patent Application Ser. No. 61/097,328, entitled "14-HYDROXY-DOCOSAHEXANAENOIC ACID COMPOUNDS", filed Sep. 16, 2008, the contents of which are both incorporated herein in their entirety for all purposes.

STATEMENT REGARDING FEDERALLY SPONSORED RESEARCH

The work leading to this invention was supported in part by National Institutes of Health (NIH) grants P50-DE016191 and R37-GM038765. The U.S. Government therefore may have certain rights in the invention.

FIELD OF THE INVENTION

The invention relates generally to novel dihydroxy analogues of docosahexaenoic acid (DHA) all having a hydroxyl group at C-14 of the carbon chain and a second hydroxyl group at either the C-4, C-7 or C-13 positions of the carbon chain.

BACKGROUND OF THE INVENTION

Given the contribution of uncontrolled inflammation to many human diseases, the identification of endogenous control mechanisms in the acute inflammatory response is of wide interest (1). Classic lipid mediators such as the prostaglandins and leukotrienes are well appreciated for their important pro-inflammatory roles in inflammation (2). In recent years, the resolution of inflammation has emerged as an area with considerable potential to contain local mediators that may be useful for new therapeutic approaches (for reviews, see 3, 4). Using an unbiased systems approach employing lipidomics, proteomics and cell trafficking to study self-resolving inflammatory exudates revealed that the termination of acute inflammation involves active biosynthetic processes producing novel endogenous lipid mediators that are both anti-inflammatory and pro-resolving (5-8). It is now clear that resolution of acute inflammation is an active rather than passive process as previously understood (9), generating novel potent counter-regulatory mediators termed resolvins and protectins (for a recent review, see Ref 4).

Resolvins and protectins are biosynthesized by exudates from essential omega-3 fatty acids (e.g., EPA and DHA), and the structures are established for key members of these families (4). The immune regulatory actions of omega-3 fatty acids and their roles in human health and diseases such as cancer and neuroinflammation are widely appreciated (10-12). Although omega-3 fatty acids are in wide use as dietary supplements and potential therapeutics in many diseases including inflammatory diseases, their mechanism(s) and connection to inflammation remain of interest. Resolvins and protectins display potent multi-level anti-inflammatory and pro-resolving actions (13) and are members of a new genus of endogenous mediators of resolution (4). For example, resolvin E1 is biosynthesized from EPA and interacts with specific receptors to control inflammatory cells (14, 15). Also, fat-1 transgenic mice, producing higher endogenous levels of omega-3, show reduced inflammatory status and elevated levels of resolvins and protectins, which when administered reduce inflammation and stimulate resolution (16-18). The main biosynthetic route with DHA for resolvins and protectins proceeds during resolution via a 17S-hydroperoxydocosahexaenoic intermediate produced by a lipoxygenase mechanism. With aspirin therapy, acetylated cyclooxygenase-2 produces aspirin-triggered 17R-epimers of resolvins and protectins as well as enhances their formation (6). Genetic deficiency or overexpression of murine 12/15-LOX regulates production of resolvins and protectins and alters their responses to both thermal injury and extent of atherosclerosis (17, 18).

Therefore, a need exists for a further understanding of, an exploration or and identification of new useful materials previously not appreciated as potent biological mediators of interest.

BRIEF SUMMARY OF THE INVENTION

Evidence for a new pathway of mediators operative in resolution of acute inflammation that possess potent actions with PMN and MΦs is provided. Identification of these new mediators, coined maresins (macrophage mediators in resolving inflammation), provides evidence for autacoids produced from essential omega-3 fatty acids by a new pathway that may be linked to homeostasis, inflammation-resolution, wound healing and cancer.

Thus, the present invention provides evidence for new mediators and a pathway operative during the resolution of acute inflammation that converts DHA to a novel 14S-series of DHA analogues that possess potent dual anti-inflammatory and pro-resolving actions with both neutrophils and macrophages. Identification of these new 14S-series DHA analogues provides further evidence for local mediators produced from essential omega-3 fatty acids that may link the known beneficial actions of DHA in organ systems as well as actions reducing inflammatory disease and cancer in humans.

The present invention surprisingly provides novel compounds, compositions and methods of use pertaining to dihydroxy analogues of docosahexaenoic acid (DHA) all having a hydroxyl group at C-14 of the carbon chain and a second hydroxyl group at either the C-4, C-7 or C-14 positions of the carbon chain. These materials are biogenically derived and isolated from media.

In one embodiment, the invention pertains to a new and useful DHA analogue such as a compound comprising the formula (I):

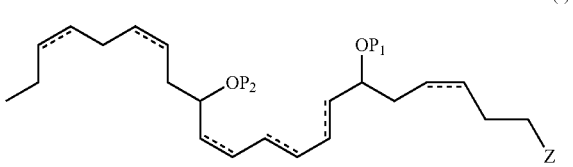

wherein each of $P_1$ and $P_2$ individually is a protecting group or a hydrogen atom;

wherein ═ is a double bond;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from ═O, —OR$^d$, (C1-C3) haloalkyloxy, —OCF$_3$, ═S, —SR$^d$, ═NR$^d$, ═NOR$^d$, —NR$^c$R$^c$, halogen, —CF$_3$, —CN, —NC, —OCN, —SCN, —NO, —NO$_2$, ═N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, provided when Z is —C(O)OR$^d$, then R$^d$ for Z is not a hydrogen. In certain aspects, P$_1$ and P$_2$ are both hydrogen atoms. In another aspect, the double bonds at the 4, 10, 16 and 19 positions are each of Z configuration or the double bonds at the 4, 16 and 19 positions are each of the Z configuration.

A particular isomer of interest of the DHA analogue (I) is (Ia) comprising the formula:

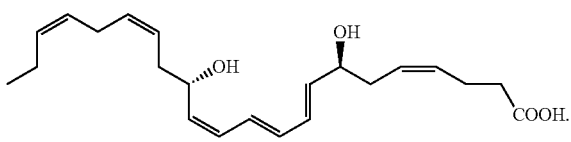

(Ia)

Another isomer of interest of the DHA analogue (I) is (Ib) comprising the formula:

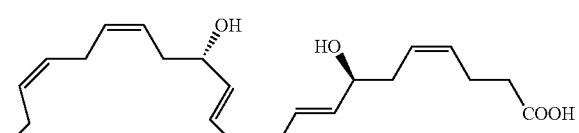

(Ib)

referred to as the "double dioxygenation" product.

It should be understood that compounds (Ia) and (Ib) include all pharmaceutically acceptable salts, esters thereof, the purified/isolated forms, as well as compounds wherein one or both of the hydroxyls are converted into a protecting group as described herein.

In another aspect, the present invention provides new and useful DHA analogues such as a purified compound comprising the formula (I):

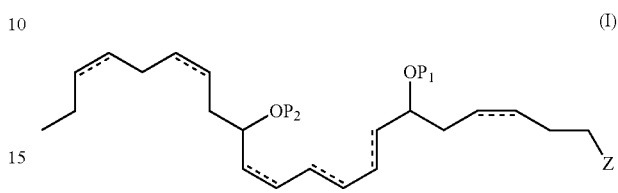

(I)

wherein P$_1$, P$_2$, ═, Z, R$^a$, R$^b$, R$^c$, R$^d$ and n are as previously defined. In one aspect, P$_1$ and P$_2$ are both hydrogen atoms. In another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Ic):

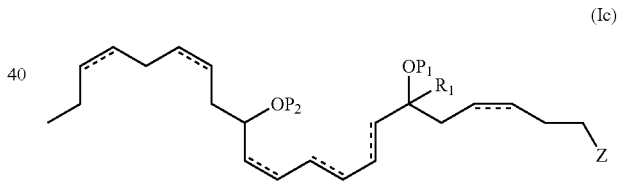

(Ic)

wherein P$_1$, P$_2$, ═, Z, R$^a$, R$^b$, R$^c$, R$^d$ and n are as previously defined. R$_1$ is selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl. In one aspect, R$_1$ is a methyl group.

In one aspect, P$_1$ and P$_2$ are both hydrogen atoms. In another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Id):

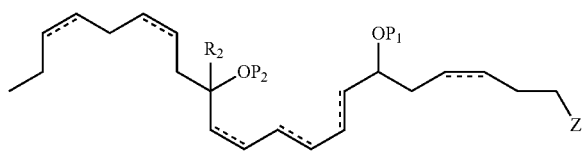

(Id)

wherein $P_1$, $P_2$, =====, Z, $R^a$, $R^b$, $R^c$, $R^d$ and n are as previously defined. $R_2$ is selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl. In one aspect, $R_2$ is a methyl group.

In one aspect, $P_1$ and $P_2$ are both hydrogen atoms. In another aspect, Z is —C(O)$OR^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Ie):

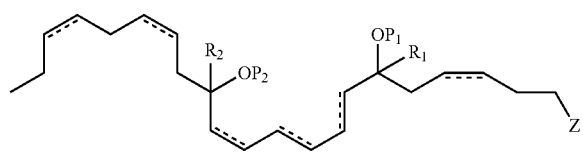

(Ie)

wherein $P_1$, $P_2$, =====, Z, $R^a$, $R^b$, $R^c$, $R^d$, $R_1$, $R_2$ and n are as previously defined.

In one aspect, $P_1$ and $P_2$ are both hydrogen atoms. In another aspect, $R_1$ and $R_2$ are both methyl groups. In still another aspect, Z is —C(O)$OR^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the invention pertains to a new and useful DHA analogue such as a compound comprising the formula (II):

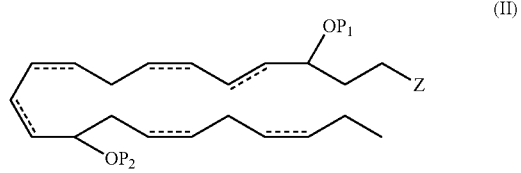

(II)

wherein $P_1$, $P_2$, =====, Z, $R^a$, $R^b$, $R^c$, $R^d$ and n are as previously defined, provided when Z is —C(O)$OR^d$, then $R^d$ for Z is not a hydrogen. In one embodiment, $P_1$ and $P_2$ are both hydrogen atoms. In another embodiment, the double bonds at the 7, 16 and 19 positions are each of Z configuration.

In another aspect, the present invention provides new and useful DHA analogues such as a purified compound comprising the formula (II):

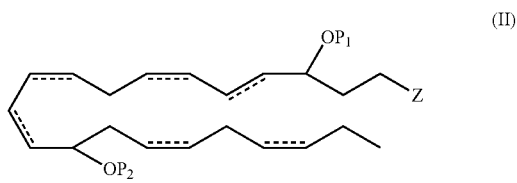

(II)

wherein $P_1$, $P_2$, =====, Z, $R^a$, $R^b$, $R^c$, $R^d$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration.

In another aspect, the present invention provides new and useful DHA analogues such as a compound comprising the formula (IIa):

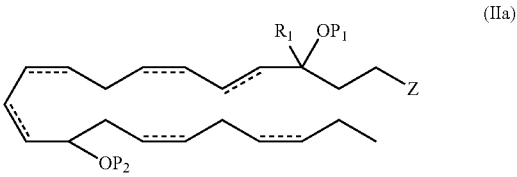

(IIa)

wherein $P_1$, $P_2$, =====, Z, $R^a$, $R^b$, $R^c$, $R^d$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration. In yet another aspect, $R_1$ is a methyl group.

In another aspect, the present invention provides new and useful DHA analogues such as a compound comprising the formula (IIb):

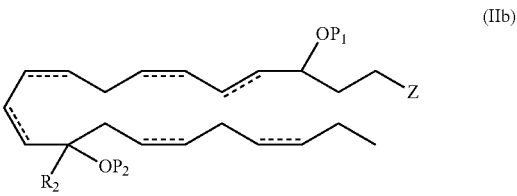

(IIb)

wherein $P_1$, $P_2$, =====, Z, $R^a$, $R^b$, $R^c$, Rd, $R_2$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration. In yet another aspect, $R_2$ is a methyl group.

In another aspect, the present invention provides new and useful DHA analogues such as a compound comprising the formula (IIc):

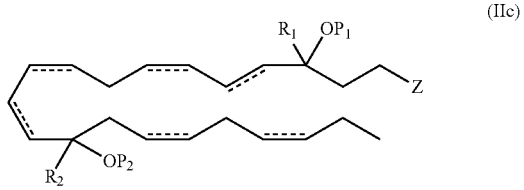

(IIc)

wherein $P_1$, $P_2$, $\text{=====}$, Z, $R^a$, $R^b$, $R^c$, Rd, $R_1$, $R_2$ and n are as previously defined. In one aspect, $P_1$ and $P_2$ are both hydrogen atoms. In another aspect, Z is —C(O)OR$^d$ and R$^d$ of Z is a hydrogen atom. In still another aspect, the double bonds at the 7, 16 and 19 positions are each of Z configuration. In yet another aspect, $R_1$ and $R_2$ are both methyl groups.

In another aspect, the present invention provides new and useful DHA analogues such as a compound comprising formula (III):

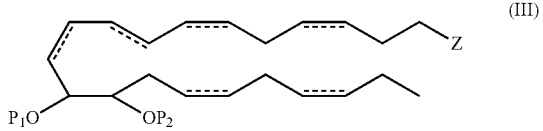

(III)

wherein $P_1$, $P_2$, $\text{=====}$, Z, $R^a$, $R^b$, $R^c$, $R^d$ and n are as previously defined, provided when Z is —C(O)OR$^d$, then R$^d$ for Z is not a hydrogen. In one embodiment, $P_1$ and $P_2$ are both hydrogen atoms. In another embodiment, the double bonds at the 4, 7, 16 and 19 positions are each of Z configuration.

In still another aspect, the present invention provides new and useful DHA analogues such as a purified compound comprising the formula (III):

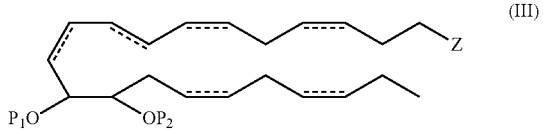

(III)

wherein $P_1$, $P_2$, $\text{=====}$, Z, $R^a$, $R^b$, $R^c$, $R^d$ and n are as previously defined. In one aspect, $P_1$ and $P_2$ are both hydrogen atoms. In another aspect, Z is —C(O)OR$^d$ and R$^d$ of Z is a hydrogen atom. In another embodiment, the double bonds at the 4, 7, 16 and 19 positions are each of Z configuration.

In still another aspect, the present invention provides new and useful DHA analogues such as a compound comprising the formula (IIa):

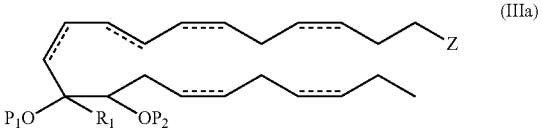

(IIIa)

wherein $P_1$, $P_2$, $\text{=====}$, Z, $R^a$, $R^b$, $R^c$, $R^d$, $R_1$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_1$ is a methyl group. In another embodiment, the double bonds at the 4, 7, 16 and 19 positions are each of Z configuration.

In still another aspect, the present invention provides new and useful DHA analogues such as a compound comprising the formula (IIIb):

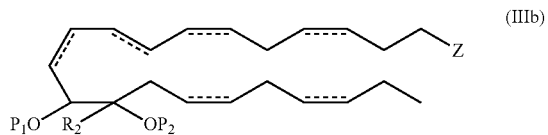

(IIIb)

wherein $P_1$, $P_2$, $\text{=====}$, Z, $R^a$, $R^b$, $R^c$, $R^d$, $R_2$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_2$ is a methyl group. In another embodiment, the double bonds at the 4, 7, 16 and 19 positions are each of Z configuration.

In still another aspect, the present invention provides new and useful DHA analogues such as a compound comprising the formula (IIIc):

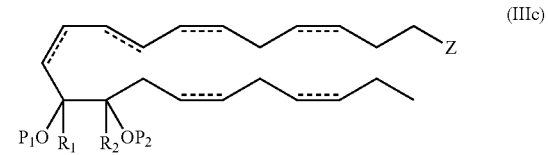

(IIIc)

wherein $P_1$, $P_2$, $\text{=====}$, Z, $R^a$, $R^b$, $R^c$, $R^d$, $R_1$, $R_2$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_1$ and $R_2$ are both methyl groups. In another embodiment, the double bonds at the 4, 7, 16 and 19 positions are each of Z configuration.

In yet another aspect, the present invention provides new and useful DHA analogues such as a compound comprising formula (IV):

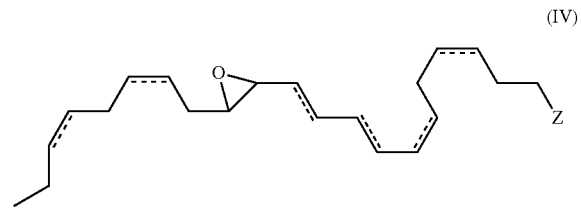

(IV)

wherein $P_1$, $P_2$, $\text{=====}$, Z, $R^a$, $R^b$, $R^c$, $R^d$ and n are as previously defined, provided when Z is —C(O)OR$^d$, then R$^d$ for Z is not a hydrogen. In one embodiment, the double bonds at the 4, 7, 16 and 19 positions are each of Z configuration.

In still another aspect, the present invention provides new and useful DHA analogues such as a purified compound comprising the formula (IV):

(IV)

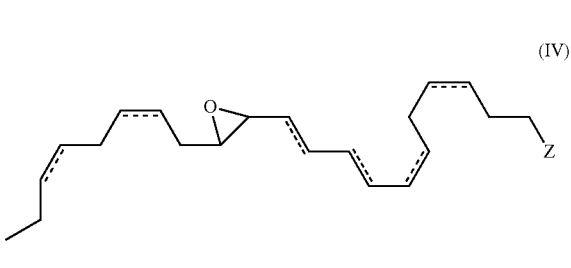

wherein ===, Z, $R^a$, $R^b$, $R^c$, $R^d$ and n are as previously defined. In an aspect, Z is —C(O)$OR^d$ and $R^d$ of Z is a hydrogen atom. In another embodiment, the double bonds at the 4, 7, 16 and 19 positions are each of Z configuration.

In another aspect, the invention provides a compound comprising the formula (V):

(V)

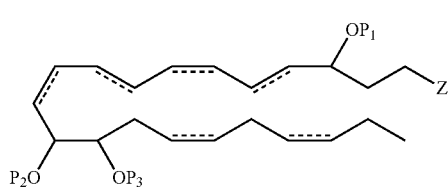

wherein each of $P_1$, $P_2$ and $P_3$ individually is a protecting group or a hydrogen atom and ===, Z, $R^a$, $R^b$, $R^c$, $R^d$ and n are as previously defined, provided when Z is —C(O)$OR^d$, then $R^d$ for Z is not a hydrogen. In one aspect, $P_1$, $P_2$ and $P_3$ are all hydrogen atoms. In another aspect, the double bonds at the 7, 16 and 19 positions are each of Z configuration.

In still yet another aspect, the present invention provides a purified compound comprising the formula (V):

(V)

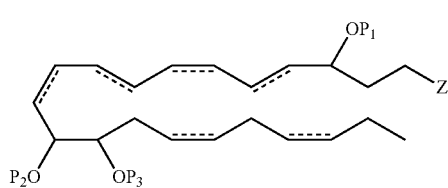

wherein $P_1$, $P_2$, $P_3$ ===, Z, $R^a$, $R^b$, $R^c$, $R^d$ and n are as previously defined. In one aspect, $P_1$, $P_2$ and $P_3$ are all hydrogen atoms. In another aspect, Z is —C(O)$OR^d$ and $R^d$ of Z is a hydrogen atom. In another embodiment, the double bonds at the 7, 16 and 19 positions are each of Z configuration.

In still yet another aspect, the present invention provides a compound comprising the formula (Va):

(Va)

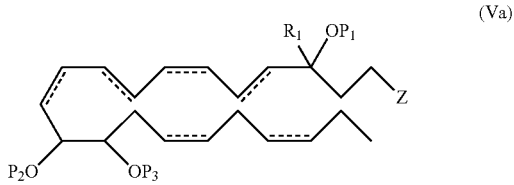

wherein $P_1$, $P_2$, $P_3$, ===, Z, $R^a$, $R^b$, $R^c$, $R^d$, $R_1$ and n are as previously defined. In one aspect, $P_1$, $P_2$ and $P_3$ are all hydrogen atoms. In another aspect, Z is —C(O)$OR^d$ and $R^d$ of Z is a hydrogen atom. In another embodiment, the double bonds at the 7, 16 and 19 positions are each of Z configuration. In still another aspect, $R_1$ is a methyl group.

In another aspect, the present invention provides a compound comprising the formula (Vb):

(Vb)

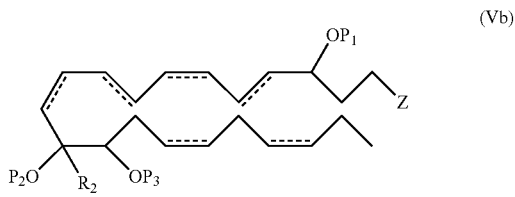

wherein $P_1$, $P_2$, $P_3$ ===, Z, $R^a$, $R^b$, $R^c$, $R^d$, $R_2$ and n are as previously defined. In one aspect, $P_1$, $P_2$ and $P_3$ are all hydrogen atoms. In another aspect, Z is —C(O)$OR^d$ and $R^d$ of Z is a hydrogen atom. In another embodiment, the double bonds at the 7, 16 and 19 positions are each of Z configuration. In still another aspect, $R_2$ is a methyl group.

In another aspect, the present invention provides a compound comprising the formula (Vc):

(Vc)

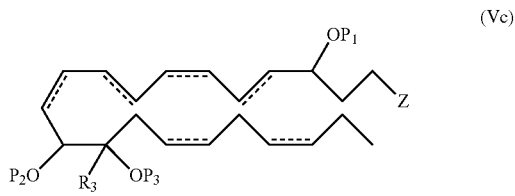

wherein $P_1$, $P_2$, $P_3$ ===, Z, $R^a$, $R^b$, $R^c$, $R^d$, $R_3$ and n are as previously defined. In one aspect, $P_1$, $P_2$ and $P_3$ are all hydrogen atoms. In another aspect, Z is —C(O)$OR^d$ and $R^d$ of Z is a hydrogen atom. In another embodiment, the double bonds at the 7, 16 and 19 positions are each of Z configuration. In still another aspect, $R_3$ is a methyl group.

In another aspect, the present invention provides a compound comprising the formula (Vd):

(Vd)

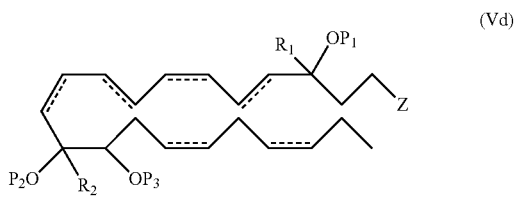

wherein $P_1$, $P_2$, $P_3$, ===, Z, $R^a$, $R^b$, $R^c$, $R^d$, $R_1$, $R_2$ and n are as previously defined. In one aspect, $P_1$, $P_2$ and $P_3$ are all hydrogen atoms. In another aspect, Z is —C(O)$OR^d$ and $R^d$ of Z is a hydrogen atom. In another embodiment, the double bonds at the 7, 16 and 19 positions are each of Z configuration. In still another aspect, $R_1$ and $R_2$ are methyl groups.

In another aspect, the present invention provides a compound comprising the formula (Ve):

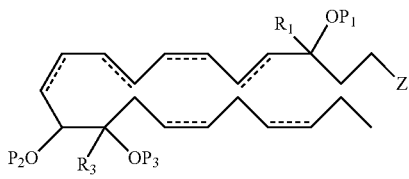

wherein $P_1$, $P_2$, $P_3$ =====, $Z$, $R^a$, $R^b$, $R^c$, $R^d$, $R_1$, $R_3$ and n are as previously defined. In one aspect, $P_1$, $P_2$ and $P_3$ are all hydrogen atoms. In another aspect, $Z$ is —C(O)OR$^d$ and R$^d$ of Z is a hydrogen atom. In another embodiment, the double bonds at the 7, 16 and 19 positions are each of Z configuration. In still another aspect, $R_1$ and $R_3$ are methyl groups.

In another aspect, the present invention provides a compound comprising the formula (Vf):

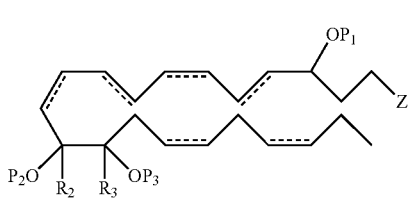

wherein $P_1$, $P_2$, $P_3$ =====, $Z$, $R^a$, $R^b$, $R^c$, $R^d$, $R_2$, $R_3$ and n are as previously defined. In one aspect, $P_1$, $P_2$ and $P_3$ are all hydrogen atoms. In another aspect, $Z$ is —C(O)OR$^d$ and R$^d$ of Z is a hydrogen atom. In another embodiment, the double bonds at the 7, 16 and 19 positions are each of Z configuration. In still another aspect, $R_2$ and $R_3$ are methyl groups.

In another aspect, the present invention provides a compound comprising the formula (Vg):

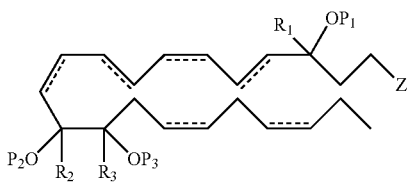

wherein $P_1$, $P_2$, $P_3$ =====, $Z$, $R^a$, $R^b$, $R^c$, $R^d$, $R_1$, $R_2$, $R_3$ and n are as previously defined. In one aspect, $P_1$, $P_2$ and $P_3$ are all hydrogen atoms. In another aspect, $Z$ is —C(O)OR$^d$ and R$^d$ of Z is a hydrogen atom. In another embodiment, the double bonds at the 7, 16 and 19 positions are each of Z configuration. In still another aspect, $R_1$, $R_2$ and $R_3$ are all methyl groups.

In another aspect, the present invention provides new and useful DHA analogues such as a purified compound comprising the formula (VI):

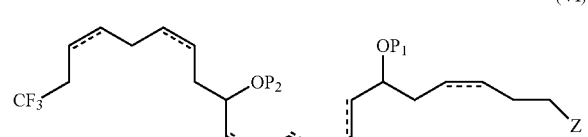

wherein $P_1$, $P_2$, =====, $Z$, $R^a$, $R^b$, $R^c$, $R^d$ and n are as previously defined.

In one aspect, $P_1$ and $P_2$ are both hydrogen atoms. In another aspect, $Z$ is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a compound comprising the formula (VIa):

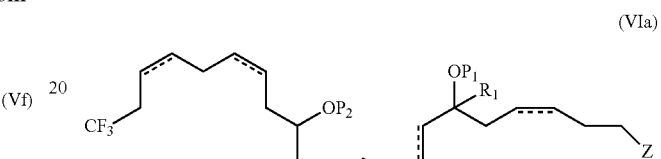

wherein $P_1$, $P_2$, =====, $Z$, $R^a$, $R^b$, $R^c$, $R^d$, $R_1$ and n are as previously defined. In one aspect, $R_1$ is a methyl group.

In one aspect, $P_1$ and $P_2$ are both hydrogen atoms. In another aspect, $Z$ is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as compound comprising the formula (VIb):

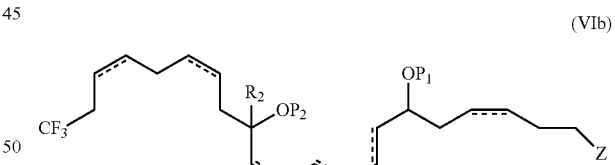

wherein $P_1$, $P_2$, =====, $Z$, $R^a$, $R^b$, $R^c$, $R^d$, $R_2$ and n are as previously defined. In one aspect, $R_2$ is a methyl group.

In one aspect, $P_1$ and $P_2$ are both hydrogen atoms. In another aspect, $Z$ is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a compound comprising the formula (VIc):

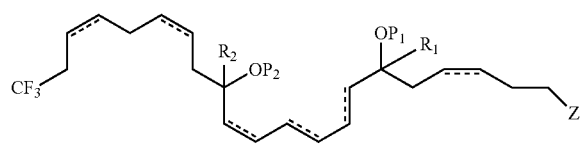

(VIc)

wherein $P_1$, $P_2$, ====, Z, $R^a$, $R^b$, $R^c$, $R^d$, $R_1$, $R_2$ and n are as previously defined.

In one aspect, $P_1$ and $P_2$ are both hydrogen atoms. In another aspect, $R_1$ and $R_2$ are both methyl groups. In still another aspect, Z is —C(O)$OR^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the C-14 alcohol has an S configuration for the compounds noted throughout the application.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

In yet another aspect, the present invention is drawn to methods for treating or preventing inflammation or inflammatory disease in a mammal. The method involves administering a prophylactically or therapeutically effective amount of at least one compound of the invention, or a pharmaceutical composition thereof. For example, the compounds of the invention can be used to treat or prevent inflammation, cancer, neurodegeneration, memory loss, wrinkles, psoriasis, dandruff or dermatitis by administering to an individual in need thereof, an effective amount of any of the compounds described herein.

Additionally, the compounds of the invention can be used to neural development, fetal development, homeostasis, tissue remodeling, or wound repair by administering to an individual in need thereof, an effective amount of any of the compounds described herein.

Additional features and advantages of the invention will become more apparent from the following detailed description and claims.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIGS. 1A, 1B and 1C. Self-resolving acute inflammatory exudates. FIG. 1A. Time course of PMN (dotted line) accumulation, resolution and HDHA formation during zymosan-initiated peritonitis. Exudates were extracted for targeted lipidomics using LC/MS/MS. Hydroxydocosahexaenoic acids, 17-HDHA (dashed line) and 14S-HDHA (solid) identified using MRM results are representative (n=3) and PMN n=4. FIGS. 1B and 1C. Representative mass spectra 17-HDHA (Panel B) and 14S-HDHA (Panel C), n=3.

FIGS. 2A, 2B and 2C. Macrophages generate novel products. FIG. 2A. Murine resident MΦs (5×10$^6$ cells/ml) incubated with DHA or 14S-HpDHA: targeted LC/MS/MS-based mediator lipidomics. Selected ion chromatogram (m/z 359/250) of 7,14-dihydroxydocosahexaenoic acid (II) and its trans conjugated isomer (I). Selected ion chromatogram (dashed overlay; m/z 359/250) shows double dioxygenation product 7S,14S-diHDHA. Inset: FACS of isolated resident MΦs. FIG. 2 Panel B. Lipid mediator lipidomics. Mass spectra for 7,14-dihydroxydocosahexaenoic acid (m/z 359) and (Panel C) corresponding isomer. See inset and text for diagnostic ions n=3.

FIGS. 3A, 3B and 3C. Anti-inflammatory novel macrophage products. FIG. 3A. Reduction in PMN murine peritonitis. Activity in methyl formate fractions from C18 extraction of isolated MΦs (black), MΦ product (20 ng/mouse) isolated with RP-HPLC, PD1 (20 ng/mouse), or RvE1 (20 ng/mouse). Results are expressed as exudate PMN mean±SEM (n=3, *, p<0.05, compared to zymosan plus vehicle). FIG. 3B Differential PMN vs. monocyte actions. Mice were injected with the double dioxygenation product (0.1 ng/mouse), MΦ isolate (0.1 ng/mouse), or vehicle alone (as in Panel A), followed by i.p injection of zymosan (1 mg) to evoke peritonitis. After 2 h, leukocytes were enumerated. Black bar, PMN; hatched bar, mononuclear cells. Results are mean±SEM (n=3, *, p<0.05, compared to zymosan plus vehicle; †, p<0.05, double dioxygenation versus MΦ isolate). FIG. 3C. Reduction in peritonitis: Dose response. MΦs product isolated following HPLC isolation was injected i.v. ~2 min before i.p. zymosan. Results are mean±SEM (n=3, *, p<0.05, compared to zymosan plus vehicle).

FIG. 10 depicts Structures, LC-MS and GC-MS fragmentation for novel 14-series compounds identified using mediator-based lipidomics. [a] LC-MS/MS analysis was performed with an Agilent 1100 series HPLC coupled to an ABI Sciex Instruments 3200 Qtrap linear ion trap quadrupole mass spectrometer equipped with an Agilent Eclipse Plus C18 column (4.6 mm×50 mm×1.8 μm). The mobile phase consisted of methanol/water/acetic acid (60/40/0.01;v/v/v) and was ramped to 80/20/0.1 (v/v/v) over 7.5 minutes and to 95/5/0.01 (v/v/v) over the next 4.5 minutes at a flow rate of 400 µl/min. The flow rate was decreased to 200 µl/min for 3 minutes, then returned to 400 µl/min and the mobile phase was ramped up over the next 6 minutes to 100/0/0.01 (v/v/v) before returning to 60/40/0.01 (v/v/v). [b] GC-MS analysis was performed with an Agilent HP6890 equipped with a HP5973N mass detector. A HP-5MS column (30 m×0.25 mm×0.25 µm) was employed with a temperature program; the initial temperature was 150° C., followed by 230° C. (8 min) and 280° C. (10 min) with a helium flow rate of 1.0 ml/min. Trimethylsilyl derivatives were prepared following treatment with diazomethane. C Spectra were recorded in methanol using an Agilent 4682 UV-Vis spectrophotometer or an Agilent 1100 series DAD. *Stereochemistries shown are tentative assignments. Double bond geometries are shown in likely configurations based on proposed biosynthetic pathways.

DETAILED DESCRIPTION

Figure 1B:
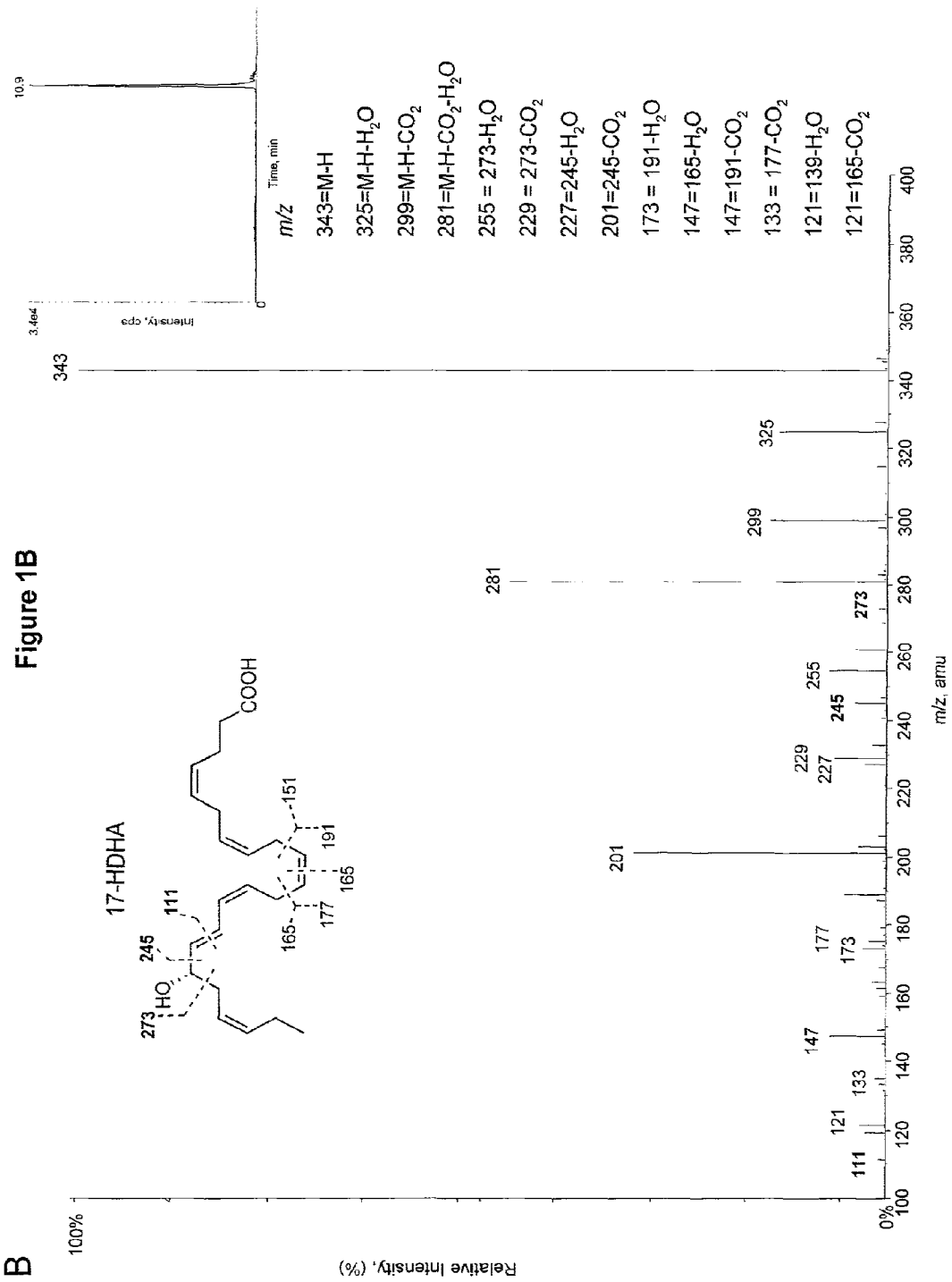

The endogenous cellular and molecular mechanisms that control acute inflammation and its resolution are of wide interest. Using self-resolving inflammatory exudates and lipidomics, a new pathway involving biosynthesis of potent anti-inflammatory and pro-resolving mediators from essential fatty acid docosahexaenoic acid (DHA) by macrophages was identified. During the resolution of murine peritonitis, exudates accumulated both 17-HDHA, a known marker of 17S-D-series resolvin and protectin biosynthesis, and 14S-HDHA from endogenous DHA. Addition of either DHA or 14S-hydroperoxydocosa-4Z,7Z,10Z,12E,16Z,19Z-hexaenoic acid (14S-HpDHA) to activated macrophages converted these substrates to novel dihydroxy-containing products that possessed potent anti-inflammatory and pro-resolving activity with a potency similar to resolvin E1 and protectin D1. Stable isotope incorporation, intermediate trapping, and characterization of physical and biological properties of the products demonstrated a novel 14-lipoxygenase pathway, generating bioactive 7,14-dihydroxy-docosa-4Z,8,10,12,16Z,19Z-hexaenoic acid, coined maresin (macrophage mediator in resolving inflammation: MaR), which enhances resolution. These findings provide that maresins and this new metabolome are involved in some of the beneficial actions of DHA and macrophages in tissue homeostasis, inflammation-resolution, wound healing and host defense.

Abbreviations used throughout the specification:
7S,14S-diHDHA (double dioxygenation), 7S,14S-dihydroxydocosa-4Z,8E,10Z,12E,16Z,19Z-hexaenoic acid
14S-HDHA, 14S-hydroxydocosa-4Z,7Z,10Z,12E,16Z, 19Z-hexaenoic acid
14S-HpDHA, 14S-hydroperoxydocosa-4Z,7Z,10Z,12E, 16Z,19Z-hexaenoic acid
17S-HDHA, 17S-hydroxydocosa-4Z,7Z,10Z,13Z,15E, 19Z-hexaenoic acid
DHA, docosahexaenoic acid
GC-MS, gas chromatography-mass spectrometry
LC/MS/MS, liquid chromatography-tandem mass spectrometry
LOX, lipoxygenase
MaR, Maresin, macrophage mediator in resolving inflammation
MΦ, macrophage
PD1, Protectin D1, 10R,17S-dihydroxydocosa-4Z,7Z, 11E,13E,15Z,19Z-hexaenoic acid
PGE$_2$, prostaglandin E$_2$
PMN, polymorphonuclear neutrophils
Rv, resolvin
RvD1, Resolvin D1, 7S,8R,17S trihydroxydocosa-4Z,9E, 11E,13Z,15E,19Z-hexaenoic acid
RvE1, Resolvin E1, 5S,12R,18R-trihydroxyeicosa-6Z, 8E,10E,14Z,16E-pentaenoic acid In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Compounds of the invention" refers to the di-hydroxy, trihydroxy, and/or epoxide DHA analogues and compounds encompassed by generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature.

The compounds depicted throughout the specification contain ethylenically unsaturated sites. Where carbon carbon double bonds exist, the configurational chemistry can be either cis (Z) or trans (E) and the depictions throughout the specification are not meant to be limiting. The depictions are, in general, presented based upon the configurational chemistry of related DHA or EPA compounds, and although not to be limited by theory, are believed to possess similar configuration chemistry. The use of ≕ reflects this throughout the specification and claims so that both cis and trans isomers are contemplated. In certain embodiments the configuration of the ethylenic bond is known and is particularly described.

In one aspect of the invention, the compound(s) of the invention are substantially purified and/or isolated by techniques known in the art. The purity of the purified compounds is generally at least about 90%, preferably at least about 95%, and most preferably at least about 99% by weight.

Thus, the term "purified" as used herein does not require absolute purity; rather, it is intended as a relative term. For example, a purified DHA analogue can be one in which the subject DHA analogue is at a higher concentration than the analogue would be in its natural environment within an organism. For example, a DHA analogue of the invention can be considered purified if the analogue content in the preparation represents at least 50%, 60%, 70%, 80%, 85%, 90%, 92%, 95%, 98%, or 99% of the total analogue content of the preparation.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 µM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Electronegative group" is a chemical group that tends to acquire rather than lose electrons in its chemical interactions. Examples of electronegative groups include, but are not limited to, —$NO_2$, ammonium salts, sulfonyl groups, carbonyl groups, halogens, esters, carboxylic acids, nitriles, etc.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts formed when an basic proton is present in the parent compound such as acid addition salts, formed with inorganic acids such as hydrochloric acid, hydrobromic acid, sulfuric acid, nitric acid, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant, excipient or carrier with which a compound of the invention is administered.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphonyl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2.sup.nd ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by inflammation, inflammatory responses, vasoconstriction and myeloid suppression. Examples of subjects include humans, dogs, cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl(isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl(propano); butan-1,4-diyl(butano); and the like (also referred to as alkylenos, defined infra).

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra)

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteratoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indene, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or spa carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

The present invention is also drawn to methods for treating arterial inflammation, arthritis, psoriasis, urticara, vasculitis, asthma, ocular inflammation, pulmonary inflammation, pulmonary fibrosis, seborrheic dermatitis, pustular dermatosis, or cardiovascular diseases in a subject by administration of one or more of the DHA analogs described herein. Disease states or conditions that are associated with inflammation such as the recruitment of neutrophils, leukocytes and/or cytokines are included within the general scope of inflammation and include, for example, Addiction, AIDS, Alcohol-related disorders, Allergy, Alzheimer's disease, Anesthesiology, Anti-infectives, Anti-inflammatory agents, Arthritis, Asthma, Atherosclerosis, Bone diseases, Breast cancer, Cancer, Cardiovascular diseases, Child health, Colon cancer, Congenital defects, Decision analysis, Degenerative neurologic disorders, Dementia, Dermatology, Diabetes mellitus, Diagnostics, Drug delivery, Drug discovery/screen, Endocrine disorders, ENT, Epidemiology, Eye diseases, Fetal and maternal medicine, Gastrointestinal disorders, Gene therapy, Genetic diagnostics, Genetics, Genitourinary disorders, Geriatric medicine, Growth and Development, Hearing, Hematologic disorders, Hepatobiliary disorders, Hypertension, Imaging, Immunology, Infectious diseases, Leukemia/lymphoma, Lung cancer, Metabolic disorders, Neonatology, Neurological disorders, Neuromuscular disorders, Nuclear medicine, Obesity/eating disorders, Orthopedic, Other, Parasitic diseases, Perinatal disorders, Pregnancy, Preventative medicine, Prostate cancer, Psychiatric disorders, Pulmonary disorders, Radiology, Renal disorders, Reproduction, Rheumatic diseases, Stroke, Surgical, Transplantation, Vaccines, Vascular medicine, Wound healing, oral infections, periodontal disease, brain injury, trauma and neuronal inflammation, and Women's health.

The pharmaceutical compositions of the invention include a "therapeutically effective amount" or a "prophylactically effective amount" of one or more of the DHA analogs of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the DHA analog may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the DHA analog and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DHA analog of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one DHA analog, in combination with a pharmaceutically acceptable carrier.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1 19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The invention features an article of manufacture that contains packaging material and DHA analog formulation contained within the packaging material. This formulation contains an at least one DHA analog and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable DHA analogs are described herein.

The present invention surprisingly provides novel compounds, compositions and methods of use pertaining to dihydroxy analogues of docosahexaenoic acid (DHA) all having a hydroxyl group at C-14 of the carbon chain and a second hydroxyl group at either the C-4, C-7 or C-14 positions of the carbon chain. These materials are biogenically derived and isolated from media.

In one embodiment, the invention pertains to a new and useful DHA analogue such as a compound comprising the formula (I):

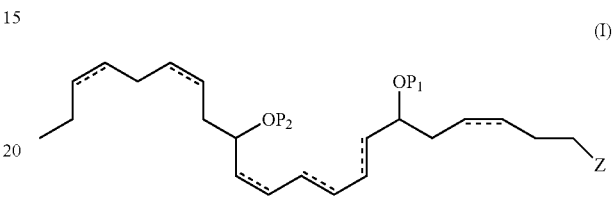

(I)

wherein each of $P_1$ and $P_2$ individually is a protecting group or a hydrogen atom;

wherein ═══ is a double bond;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from ═O, —OR$^d$, (C1-C3) haloalkyloxy, —OCF$_3$, ═S, —SR$^d$, ═NR$^d$, ═NOR$^d$, —NR$^c$R$^c$, halogen, —CF$_3$, —CN, —NC, —OCN, —SCN, —NO, —NO$_2$, ═N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof, provided when Z is —C(O)OR$^d$, then R$^d$ for Z is not a hydrogen. In certain aspects, $P_1$ and $P_2$ are both hydrogen atoms. In another aspect, the double bonds at the 4, 10, 16 and 19 positions are each of Z configuration or the double bonds at the 4, 16 and 19 positions are each of the Z configuration.

A particular isomer of interest of the DHA analogue (I) is (Ia) comprising the formula:

(Ia)

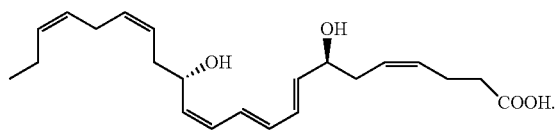

Another isomer of interest of the DHA analogue (I) is (Ib) comprising the formula:

(Ib)

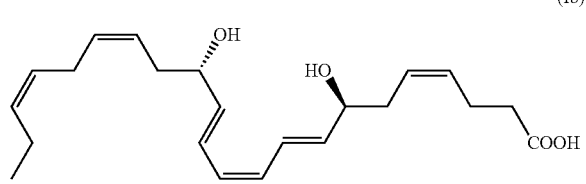

referred to as the "double dioxygenation" product.

It should be understood that compounds (Ia) and (Ib) include all pharmaceutically acceptable salts, esters thereof, the purified/isolated forms, as well as compounds wherein one or both of the hydroxyls are converted into a protecting group as described herein.

In another aspect, the present invention provides new and useful DHA analogues such as a purified compound comprising the formula (I):

(I)

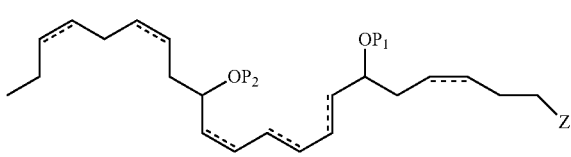

wherein $P_1$, $P_2$, =====, Z, $R^a$, $R^b$, $R^c$, $R^d$ and n are as previously defined. In one aspect, $P_1$ and $P_2$ are both hydrogen atoms. In another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Ic):

(Ic)

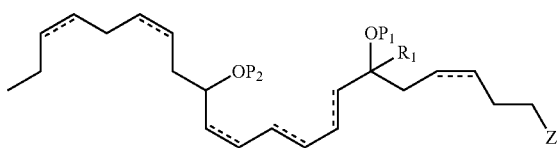

wherein $P_1$, $P_2$, =====, Z, $R^a$, $R^b$, $R^c$, $R^d$ and n are as previously defined. $R_1$ is selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl. In one aspect, $R_1$ is a methyl group.

In one aspect, $P_1$ and $P_2$ are both hydrogen atoms. In another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Id):

(Id)

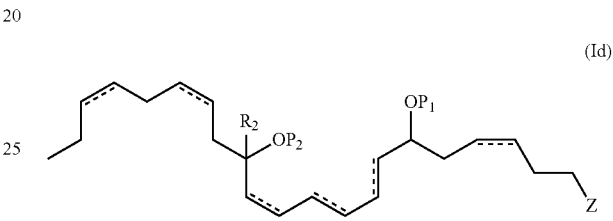

wherein $P_1$, $P_2$, =====, Z, $R^a$, $R^b$, $R^c$, $R^d$ and n are as previously defined. $R_2$ is selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl. In one aspect, $R_2$ is a methyl group.

In one aspect, $P_1$ and $P_2$ are both hydrogen atoms. In another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a purified compound comprising the formula (Ie):

(Ie)

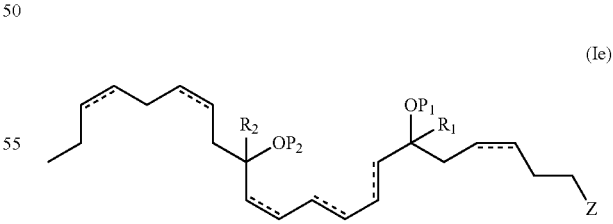

wherein $P_1$, $P_2$, =====, Z, $R^a$, $R^b$, $R^c$, $R^d$, $R_1$, $R_2$ and n are as previously defined.

In one aspect, $P_1$ and $P_2$ are both hydrogen atoms. In another aspect, $R_1$ and $R_2$ are both methyl groups. In still another aspect, Z is —C(O)OR$^d$ and R$^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the invention pertains to a new and useful DHA analogue such as a compound comprising the formula (II):

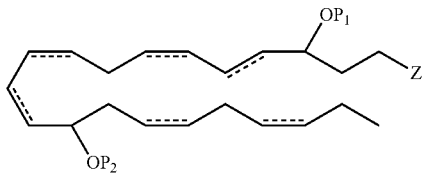
(II)

wherein $P_1$, $P_2$, =====, Z, $R^a$, $R^b$, $R^c$, $R^d$ and n are as previously defined, provided when Z is —C(O)$OR^d$, then $R^d$ for Z is not a hydrogen. In one embodiment, $P_1$ and $P_2$ are both hydrogen atoms. In another embodiment, the double bonds at the 7, 16 and 19 positions are each of Z configuration.

In another aspect, the present invention provides new and useful DHA analogues such as a purified compound comprising the formula (II):

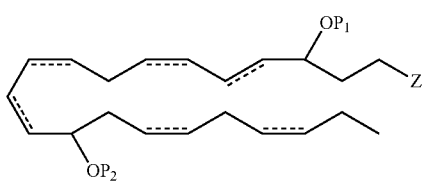
(II)

wherein $P_1$, $P_2$, =====, Z, $R^a$, $R^b$, $R^c$, $R^d$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration.

In another aspect, the present invention provides new and useful DHA analogues such as a compound comprising the formula (IIa):

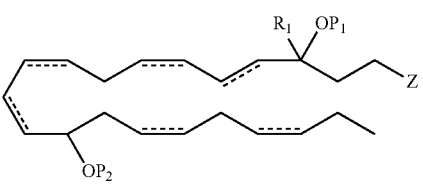
(IIa)

wherein $P_1$, $P_2$, =====, Z, $R^a$, $R^b$, $R^c$, Rd, $R_1$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration. In yet another aspect, $R_1$ is a methyl group.

In another aspect, the present invention provides new and useful DHA analogues such as a compound comprising the formula (IIb):

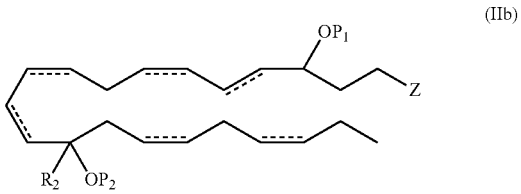
(IIb)

wherein $P_1$, $P_2$, =====, Z, $R^a$, $R^b$, $R^c$, Rd, $R_2$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration. In yet another aspect, $R_2$ is a methyl group.

In another aspect, the present invention provides new and useful DHA analogues such as a compound comprising the formula (IIc):

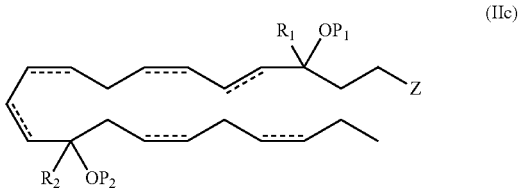
(IIc)

wherein $P_1$, $P_2$, =====, Z, $R^a$, $R^b$, $R^c$, Rd, $R_1$, $R_2$ and n are as previously defined. In one aspect, $P_1$ and $P_2$ are both hydrogen atoms. In another aspect, Z is —C(O)$OR^d$ and $R^d$ of Z is a hydrogen atom. In still another aspect, the double bonds at the 7, 16 and 19 positions are each of Z configuration. In yet another aspect, $R_1$ and $R_2$ are both methyl groups.

In another aspect, the present invention provides new and useful DHA analogues such as a compound comprising formula (III):

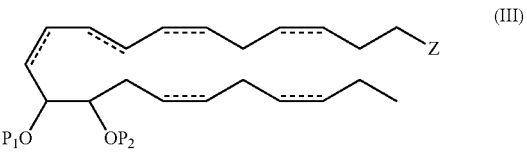
(III)

wherein $P_1$, $P_2$, =====, Z, $R^a$, $R^b$, $R^c$, $R^d$ and n are as previously defined, provided when Z is —C(O)$OR^d$, then $R^d$ for Z is not a hydrogen. In one embodiment, $P_1$ and $P_2$ are both hydrogen atoms. In another embodiment, the double bonds at the 4, 7, 16 and 19 positions are each of Z configuration.

In still another aspect, the present invention provides new and useful DHA analogues such as a purified compound comprising the formula (III):

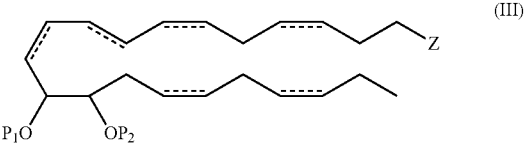
(III)

wherein $P_1$, $P_2$, =====, Z, $R^a$, $R^b$, $R^c$, $R^d$ and n are as previously defined. In one aspect, $P_1$ and $P_2$ are both hydrogen atoms. In another aspect, Z is —C(O)OR$^d$ and R$^d$ of Z is a hydrogen atom. In another embodiment, the double bonds at the 4, 7, 16 and 19 positions are each of Z configuration.

In still another aspect, the present invention provides new and useful DHA analogues such as a compound comprising the formula (IIIa):

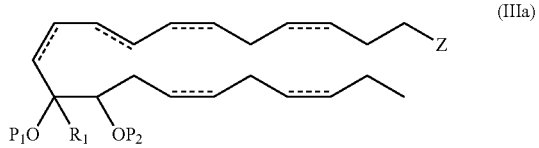
(IIIa)

wherein $P_1$, $P_2$, =====, Z, $R^a$, $R^b$, $R^c$, $R^d$, $R_1$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_1$ is a methyl group. In another embodiment, the double bonds at the 4, 7, 16 and 19 positions are each of Z configuration.

In still another aspect, the present invention provides new and useful DHA analogues such as a compound comprising the formula (IIIb):

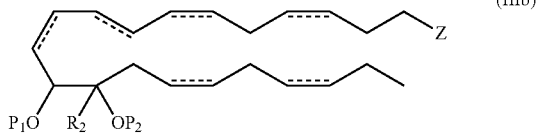
(IIIb)

wherein $P_1$, $P_2$, =====, Z, $R^a$, $R^b$, $R^c$, $R^d$, $R_2$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_2$ is a methyl group. In another embodiment, the double bonds at the 4, 7, 16 and 19 positions are each of Z configuration.

In still another aspect, the present invention provides new and useful DHA analogues such as a compound comprising the formula (IIIc):

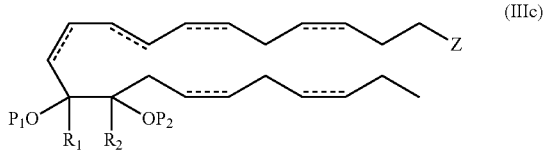
(IIIc)

wherein $P_1$, $P_2$, =====, Z, $R^a$, $R^b$, $R^c$, $R^d$, $R_1$, $R_2$ and n are as previously defined. In one aspect, $P_1$ and $P_2$ are both hydrogen atoms. In another aspect, Z is —C(O)OR$^d$ and R$^d$ of Z is a hydrogen atom. In still another aspect, $R_1$ and $R_2$ are both methyl groups. In another embodiment, the double bonds at the 4, 7, 16 and 19 positions are each of Z configuration.

In yet another aspect, the present invention provides new and useful DHA analogues such as a compound comprising formula (IV):

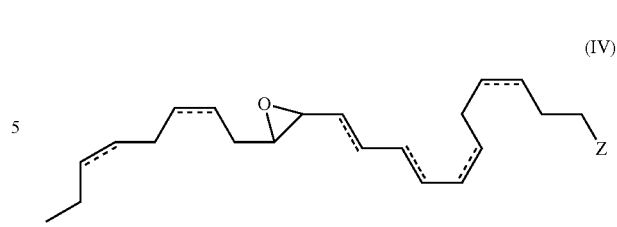
(IV)

wherein =====, Z, $R^a$, $R^b$, $R^c$, $R^d$ and n are as previously defined, provided when Z is —C(O)OR$^d$, then R$^d$ for Z is not a hydrogen. In one embodiment, the double bonds at the 4, 7, 16 and 19 positions are each of Z configuration.

In still another aspect, the present invention provides new and useful DHA analogues such as a purified compound comprising the formula (IV):

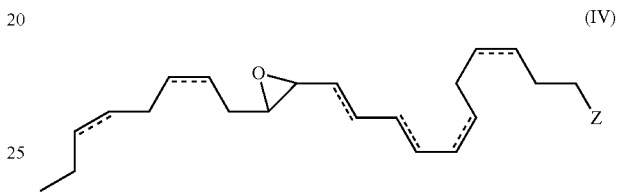
(IV)

wherein =====, Z, $R^a$, $R^b$, $R^c$, $R^d$ and n are as previously defined. In an aspect, Z is —C(O)OR$^d$ and R$^d$ of Z is a hydrogen atom. In another embodiment, the double bonds at the 4, 7, 16 and 19 positions are each of Z configuration.

In another aspect, the invention provides a compound comprising the formula (V):

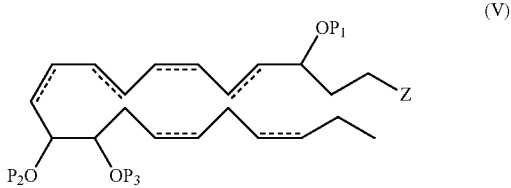
(V)

wherein each of $P_1$, $P_2$ and $P_3$ individually is a protecting group or a hydrogen atom and =====, Z, $R^a$, $R^b$, $R^c$, $R^d$ and n are as previously defined, provided when Z is —C(O)OR$^d$, then R$^d$ for Z is not a hydrogen. In one aspect, $P_1$, $P_2$ and $P_3$ are all hydrogen atoms. In another aspect, the double bonds at the 7, 16 and 19 positions are each of Z configuration.

In still yet another aspect, the present invention provides a purified compound comprising the formula (V):

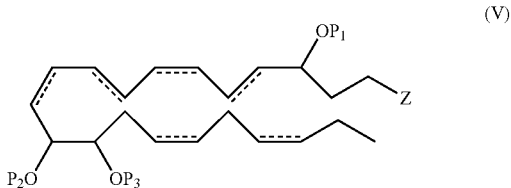
(V)

wherein $P_1$, $P_2$, $P_3$ =====, Z, $R^a$, $R^b$, $R^c$, $R^d$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration.

In still yet another aspect, the present invention provides a compound comprising the formula (Va):

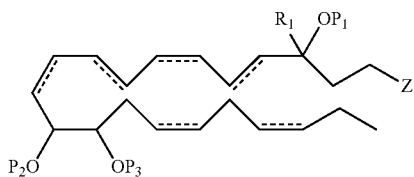

(Va)

wherein $P_1$, $P_2$, $P_3$ ====, Z, $R^a$, $R^b$, $R^c$, $R^d$, $R_1$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_1$ is a methyl group.

In another aspect, the present invention provides a compound comprising the formula (Vb):

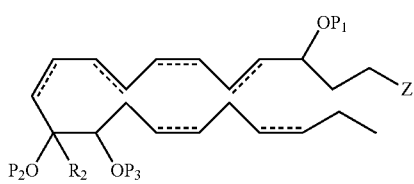

(Vb)

wherein $P_1$, $P_2$, $P_3$ ====, Z, $R^a$, $R^b$, $R^c$, $R^d$, $R_2$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_2$ is a methyl group.

In another aspect, the present invention provides a compound comprising the formula (Vc):

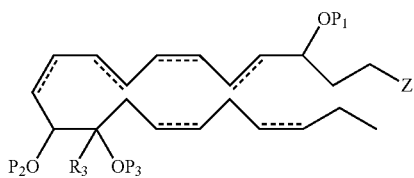

(Vc)

wherein $P_1$, $P_2$, $P_3$ ====, Z, $R^a$, $R^b$, $R^c$, $R^d$, $R_3$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_3$ is a methyl group.

In another aspect, the present invention provides a compound comprising the formula (Vd):

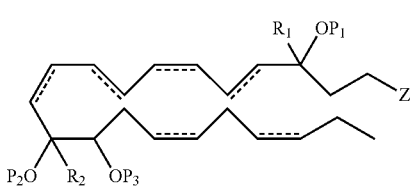

(Vd)

wherein $P_1$, $P_2$, $P_3$ ====, Z, $R^a$, $R^b$, $R^c$, $R^d$, $R_1$, $R_2$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_1$ and $R_2$ are methyl groups.

In another aspect, the present invention provides a compound comprising the formula (Ve):

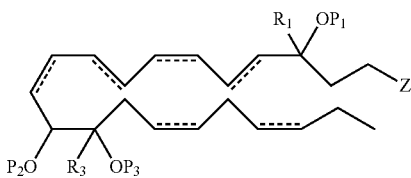

(Ve)

wherein $P_1$, $P_2$, $P_3$ ====, Z, $R^a$, $R^b$, $R^c$, $R^d$, $R_1$, $R_3$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_1$ and $R_3$ are methyl groups.

In another aspect, the present invention provides a compound comprising the formula (Vf):

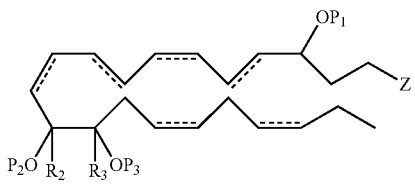

(Vf)

wherein $P_1$, $P_2$, $P_3$ ====, Z, $R^a$, $R^b$, $R^c$, $R^d$, $R_2$, $R_3$ and n are as previously defined. In one aspect, $P_1$, $P_2$ and $P_3$ are all hydrogen atoms. In another aspect, Z is —C(O)OR$^d$ and R$^d$ of Z is a hydrogen atom. In another embodiment, the double bonds at the 7, 16 and 19 positions are each of Z configuration. In still another aspect, $R_2$ and $R_3$ are methyl groups.

In another aspect, the present invention provides a compound comprising the formula (Vg):

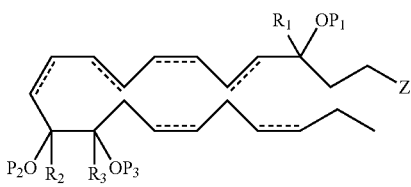

(Vg)

wherein $P_1$, $P_2$, $P_3$ =====, Z, $R^a$, $R^b$, $R^c$, $R^d$, $R_1$, $R_2$, $R_3$ and n are as previously defined. In one aspect, $P_1$, $P_2$ and $P_3$ are all hydrogen atoms. In another aspect, Z is —C(O)OR$^d$ and $R^d$ of Z is a hydrogen atom. In another embodiment, the double bonds at the 7, 16 and 19 positions are each of Z configuration. In still another aspect, $R_1$, $R_2$ and $R_3$ are all methyl groups.

In another aspect, the present invention provides new and useful DHA analogues such as a purified compound comprising the formula (VI):

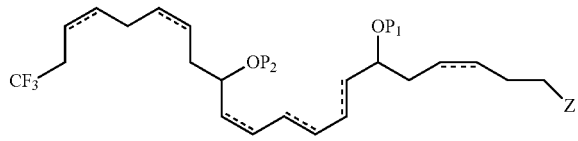

(VI)

wherein $P_1$, $P_2$, =====, Z, $R^a$, $R^b$, $R^c$, $R^d$ and n are as previously defined.

In one aspect, $P_1$ and $P_2$ are both hydrogen atoms. In another aspect, Z is —C(O)OR$^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a compound comprising the formula (VIa):

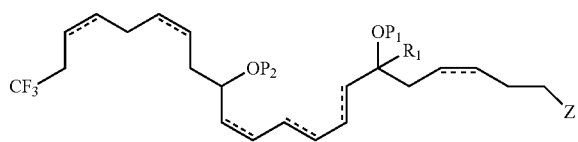

(VIa)

wherein $P_1$, $P_2$, =====, Z, $R^a$, $R^b$, $R^c$, $R^d$, $R_1$ and n are as previously defined. In one aspect, $R_1$ is a methyl group.

In one aspect, $P_1$ and $P_2$ are both hydrogen atoms. In another aspect, Z is —C(O)OR$^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a compound comprising the formula (VIb):

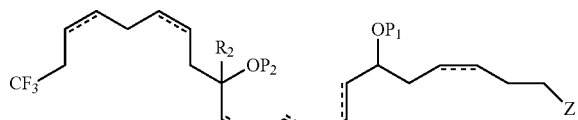

(VIb)

wherein $P_1$, $P_2$, =====, Z, $R^a$, $R^b$, $R^c$, $R^d$, $R_2$ and n are as previously defined. In one aspect, $R_2$ is a methyl group.

In one aspect, $P_1$ and $P_2$ are both hydrogen atoms. In another aspect, Z is —C(O)OR$^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the present invention provides new and useful DHA analogues such as a compound comprising the formula (VIc):

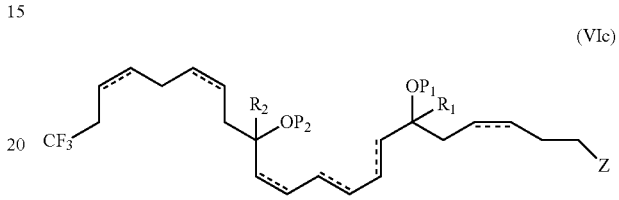

(VIc)

wherein $P_1$, $P_2$, =====, Z, $R^a$, $R^b$, $R^c$, $R^d$, $R_1$, $R_2$ and n are as previously defined.

In one aspect, $P_1$ and $P_2$ are both hydrogen atoms. In another aspect, $R_1$ and $R_2$ are both methyl groups. In still another aspect, Z is —C(O)OR$^d$ and $R^d$ of Z is a hydrogen atom. In another embodiment, the double bonds at the 4, 10, 16 and 19 positions are each of Z configuration or the double bonds at the 4, 16 and 19 positions are each of the Z configuration. In still another embodiment, the 7 hydroxyl has an S configuration. In still yet another embodiment, the 14 hydroxyl has an S configuration.

In another aspect, the C-14 alcohol has an S configuration for the compounds noted throughout the application.

It should be understood that the intermediates described herein are also included as part of the invention and can be considered active agents as well. For example, ketone containing intermediates are within the scope of the active agents as well as alkyne intermediates as described herein.

Results and Discussion

Targeted Lipidomics of Resolving Inflammatory Exudates.

Figure 1C:
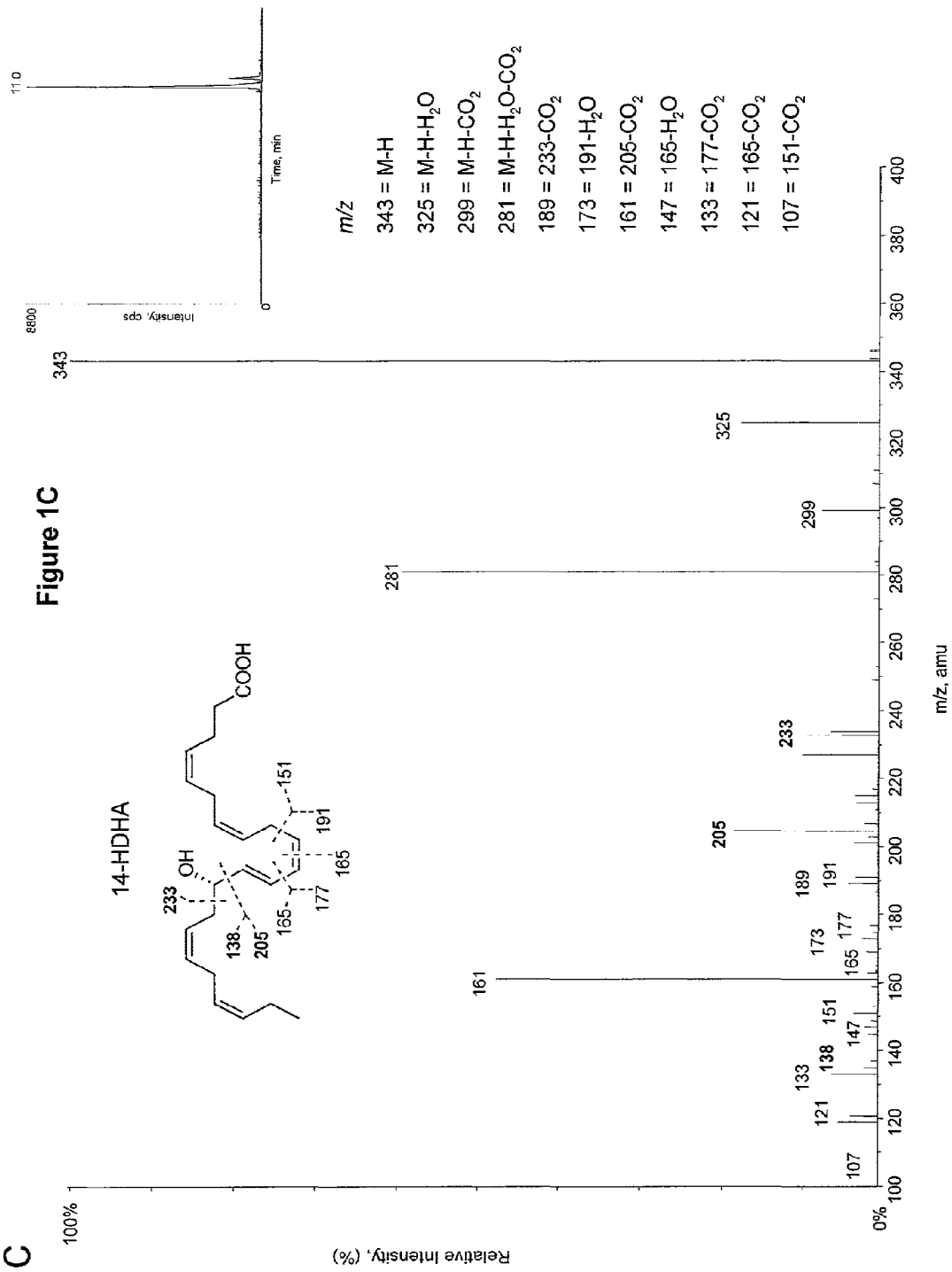

In view of the actions of specialized chemical mediators in resolution (6, 7), 17-HDHA was monitored as a biomarker of activation and conversion of endogenous DHA, as well as employed targeted lipidomics to query whether other pathways were operative (see FIG. 1). During this course of peritonitis, PMN rapidly entered, reaching max within 12 h. In this self-resolving system (19), PMN declined and were lost from exudates, thus defining resolution (FIG. 1). Unbiased targeted mediator lipidomics employing LC/MS/MS-based analyses were carried out with these exudates. In addition to 17S-HDHA, a marker of resolvin and protectin biosynthesis (6), endogenous DHA was converted to 14S-hydroxydocosahexaenoic acid (14S-HDHA). Neither product was identified in exudates obtained with the lipoxygenase (LOX) inhibitor esculetin (n=3), and both were substantially reduced in peritonitis lavages from 12/15-LOX-deficient mice (n=2, d=4). The appearance of 14S-HDHA in this system accompanied 17-HDHA throughout the 72 h course, indicating that 14S-HDHA accumulated within the resolution phase.

These two LOX products were identified by characteristic diagnostic ions in their respective mass spectra. FIG. 1B shows a representative spectrum of 17-HDHA formed in the time course, and 1C the spectrum of 14S-HDHA as well as diagnostic ions for identification. These included m/z 205, 138, and 233 specific for 14S-HDHA. The m/z 343 [M-H], m/z 325, 299, and 281 ions are shared between 14-hydroxy- and 17-hydroxydocosahexaenoic acid (see insets in FIGS. 1B and C). Both 14S-HDHA and 17-HDHA were also generated from endogenous DHA with isolated murine MΦs activated with $Ca^{2+}$ ionophore $A_{23187}$ (5.0 µM, pH 7.45, n=4; representative values: 14S-HDHA, 325 pg/$10^6$ cells; 17-HDHA, 439 pg/$10^6$ cells). These results demonstrate that during the time course of acute inflammation and its resolution a sustained production of endogenous LOX products was present in the initial acute phase at 2-4 h that accumulated during resolution with highest levels of 14S-HDHA>17-HDHA at 72 h.

Figure 2B:
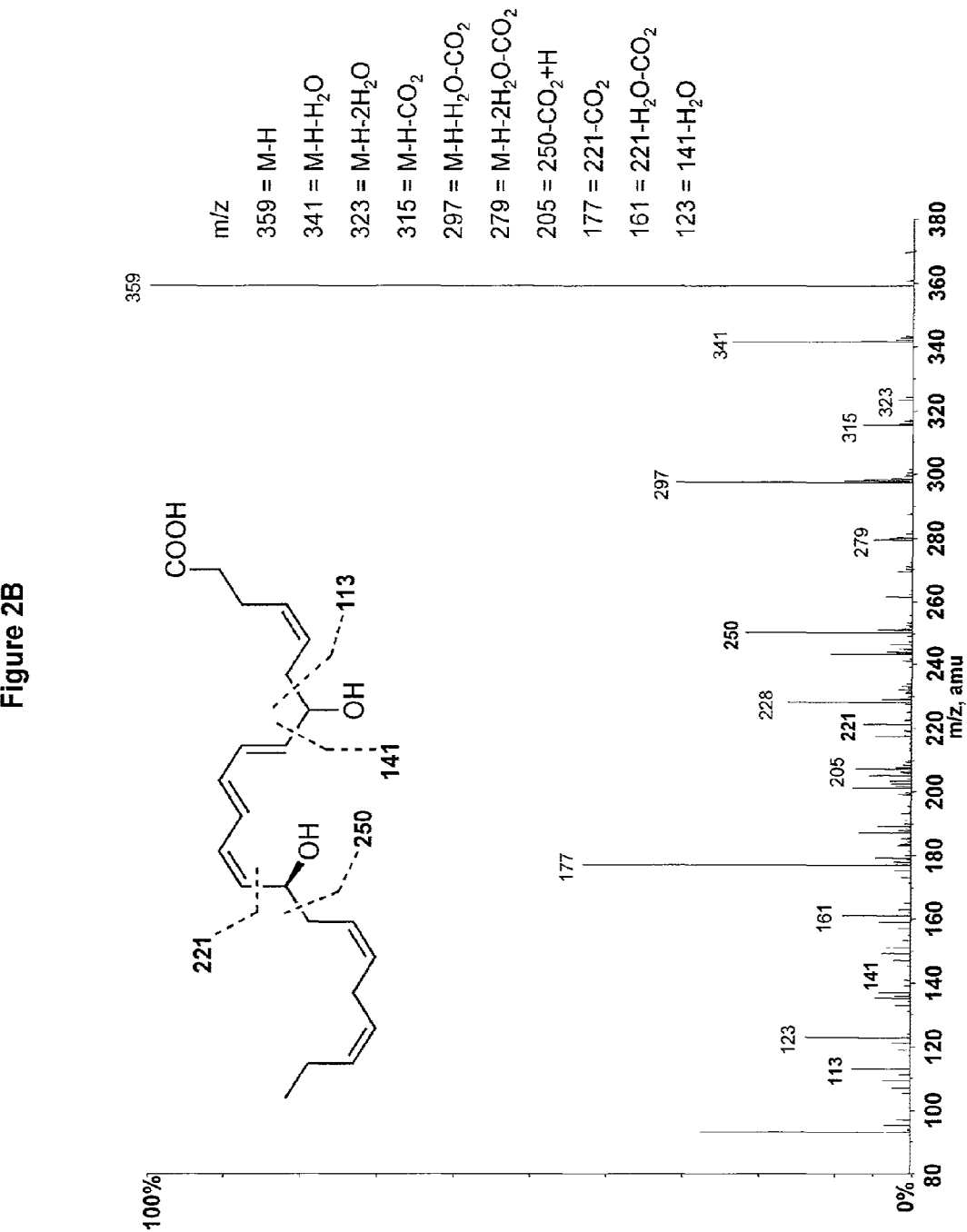
Figure 2C:
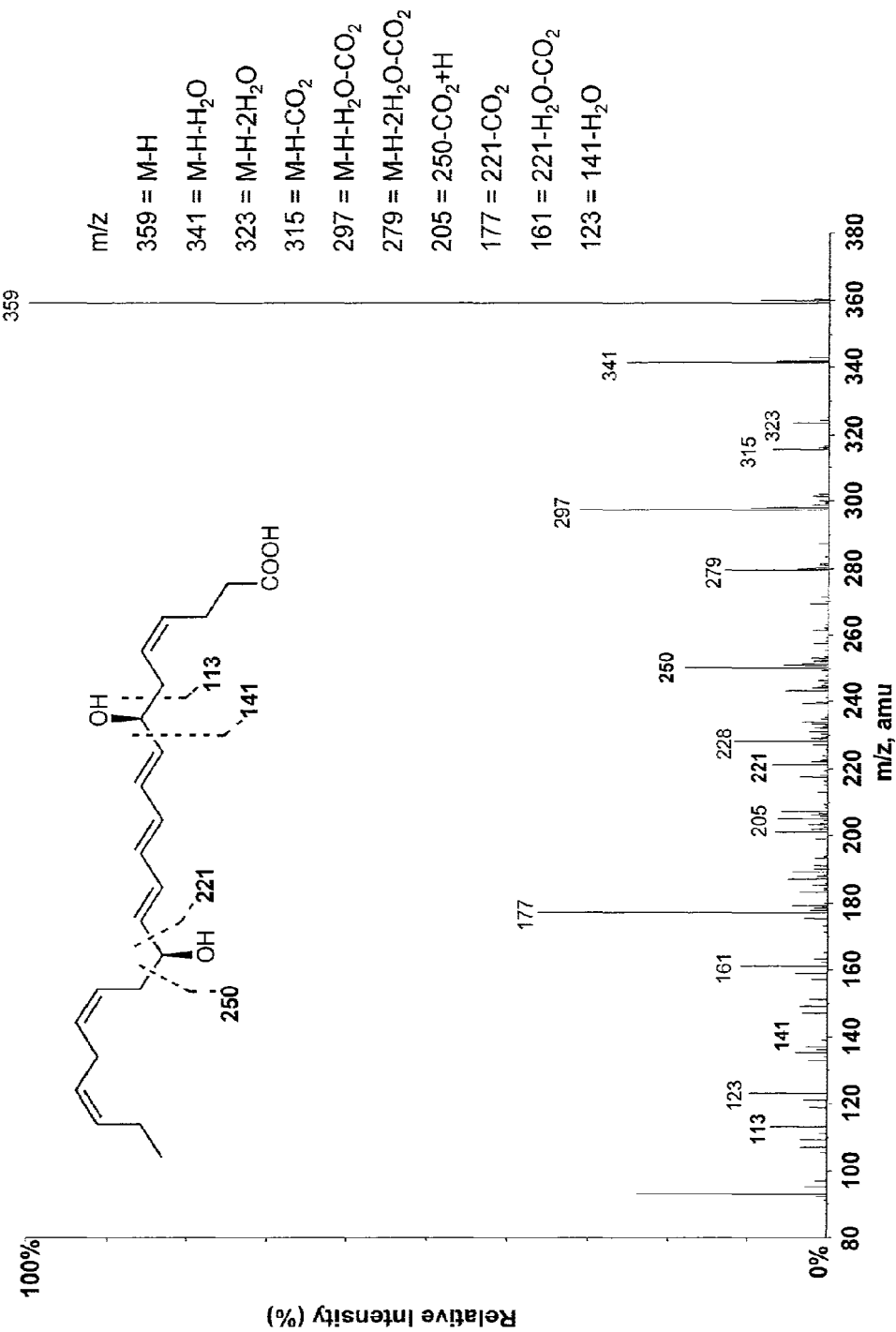

It was determined that 14S-HDHA might be a marker reflecting activation of a novel DHA (C22:6) carbon 14-lipoxygenation pathway. This could lead to production of bioactive mediators via DHA, since monohydroxy products of polyunsaturated fatty acids are biomarkers of pathways leading to potent bioactive molecules, as in the case of 17-HDHA and 17-HpDHA, precursors to resolvins and protectins (6, 20, 21). Also, 5-HETE is a well appreciated marker of arachidonic acid conversion to leukotrienes (2). To this end, resident peritoneal MΦs were isolated (see FIG. 2A, FACS inset), containing ~85-90% MΦs and 10-15% lymphocytes, and 14S-HpDHA was prepared via biogenic synthesis and incubated with these cells to determine whether it was a precursor to new bioactive products. 14S-HpDHA was isolated from 12-LOX incubated with HPLC-purified DHA (n=7) and was >98% S configuration determined by chiral LC/MS/MS. Both 14S-HpDHA (10 µM) and DHA (10 µM) were converted by resident MΦs to new products identified via LC/MS/MS-based mediator lipidomics (FIG. 2A) labeled I and II. Each had conjugated triene-containing UV chromophores, chromatographic behavior, and mass spectra consistent with 7,14-dihydroxy-containing products with a C22 backbone originating from DHA. Both gave essentially the same mass spectrum yet different retention times, indicating that they were very likely isomers (FIGS. 2B and 2C). These were isolated and subject to gas chromatography-mass spectrometry in order to further identify and confirm fragment assignments and positional sites of oxygenation, e.g., carbon positions of alcohol groups. GC-MS analyses confirmed assigned ions from LC/MS/MS and were consistent with 7,14-dihydroxy-containing products biosynthesized from DHA (FIG. 10). Isolated human MΦs incubated with 14S-HpDHA also gave the novel 7,14-dihydroxy-containing product and matched the compound from murine MΦs (n=3).

Novel Anti-Inflammatory and Pro-Resolving Mediators.

In parallel with these determinations, materials obtained from murine MΦs were assessed for potential bioactivity following extraction and C18 solid-phase chromatography. MΦ-derived material showed remarkable anti-inflammatory properties (FIG. 3A) regulating PMN entry into zymosan-induced peritonitis when directly compared to other ω-3 fatty acid-derived mediators neuroprotectin/protectin D1 (20) and RvE1 (5, 6, 14). Thus, these findings suggested that within MΦ isolates, obtained from cells incubated with 14S-hydroperoxydocosa-4Z,7Z,10Z,12E,16Z,19Z-hexaenoic acid, potent bioactive materials were biosynthesized from this precursor that regulated PMN, preventing their infiltration. These substances were likely to be very potent because only nanogram quantities given per mouse elicited anti-inflammatory actions.

Figures 3B, 3C:
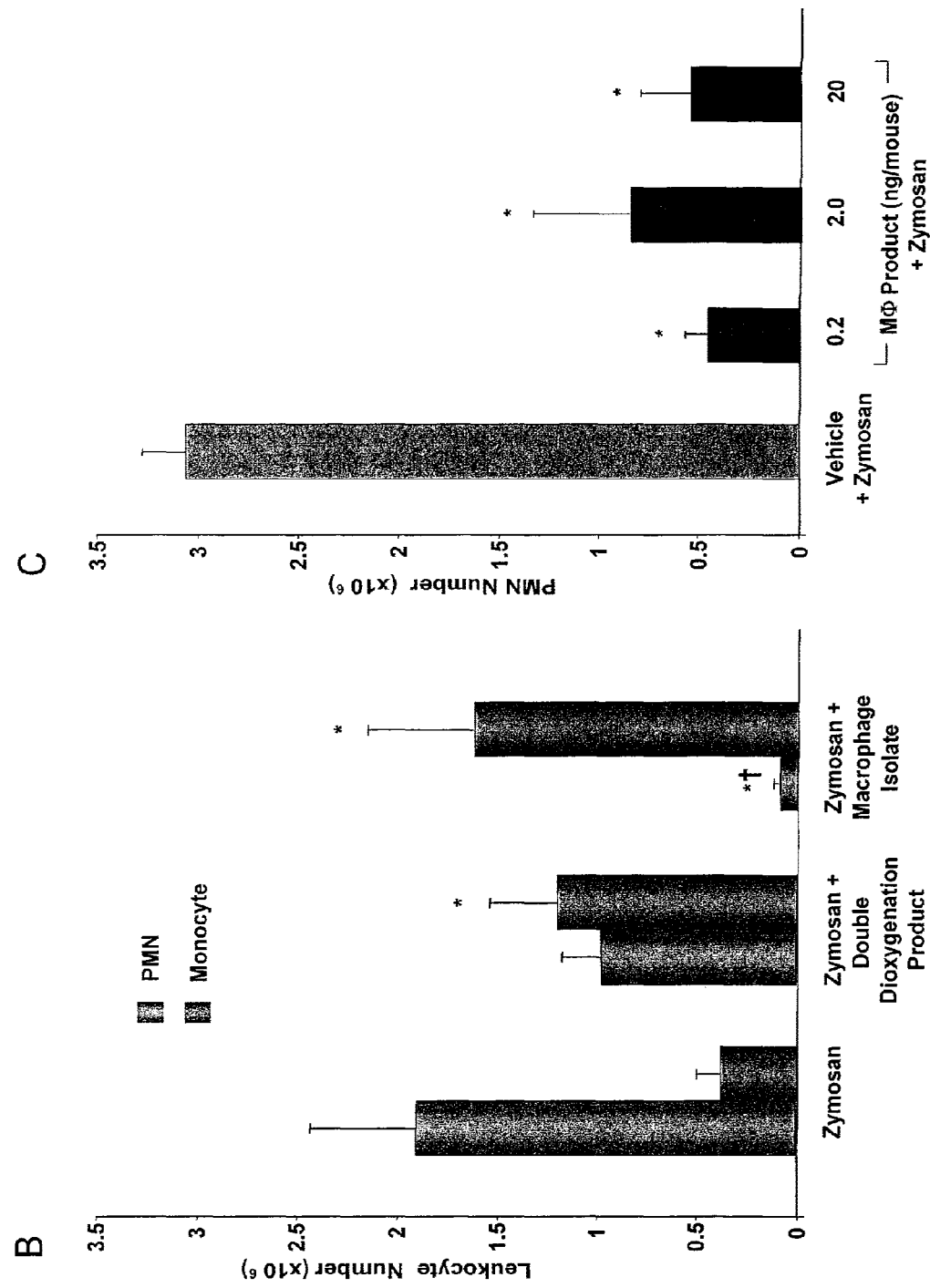

Given the ability of DHA to serve as a substrate for LOX forming both double dioxygenation products related to protectin D1 as well as the carbon 17-hydroperoxide-containing precursor of epoxide (20), it was determined that 14S-HpDHA might also be substrate for double dioxygenation. Sequential actions of 12-LOX and 5-LOX with DHA generated 7S,14S-dihydroxydocosa-4Z,8E,10Z,12E,16Z,19Z-hexaenoic acid (n=5; FIG. 2, dotted profile and FIG. 10). Likely this is an isomer of the MΦ-isolated material (FIGS. 2 and 3), because this reference compound (dotted curve in FIG. 2A) did not co-elute with MΦ-derived products beneath labels I and II. This double dioxygenation product at 0.1 ng dose per mouse reduced PMN infiltration in zymosan-induced peritonitis but appeared to be less potent than the MΦ isolated material (FIG. 3B). Thus, results in FIG. 3 clearly demonstrate potent bioactions of the novel 7,14-dihydroxy-containing product HPLC purified from resident MΦ incubations with zymosan and 14S-hydroperoxydocosa-4Z,7Z,10Z,12E,16Z,19Z-hexaenoic acid.

Further experiments were carried out to isolate material beneath peaks I and II (FIG. 2A) and determine whether compound I is an isomer of II. Subjecting the isolated compounds to isomerization conditions (22) demonstrated that compound II likely contained a cis double bond-containing triene structure sensitive to conversion to an all-trans-containing conjugated triene (i.e., 8E,10E,12E) isomer I in bench and work-up conditions. In view of $^{18}O$ incorporation and epoxide trapping (vide infra), it is likely that the isomer I peak also contained R/S racemates at carbon 7. Further RP-HPLC purification of the 7,14-dihydroxy-containing product from MΦs was carried out to assess its actions. Results in FIG. 3C demonstrate that at doses as low as 0.2 ng/mouse the new compound potently reduced infiltration of PMN into sites of inflammation.

Macrophage-Enhanced Phagocytosis.

Figure 3D:
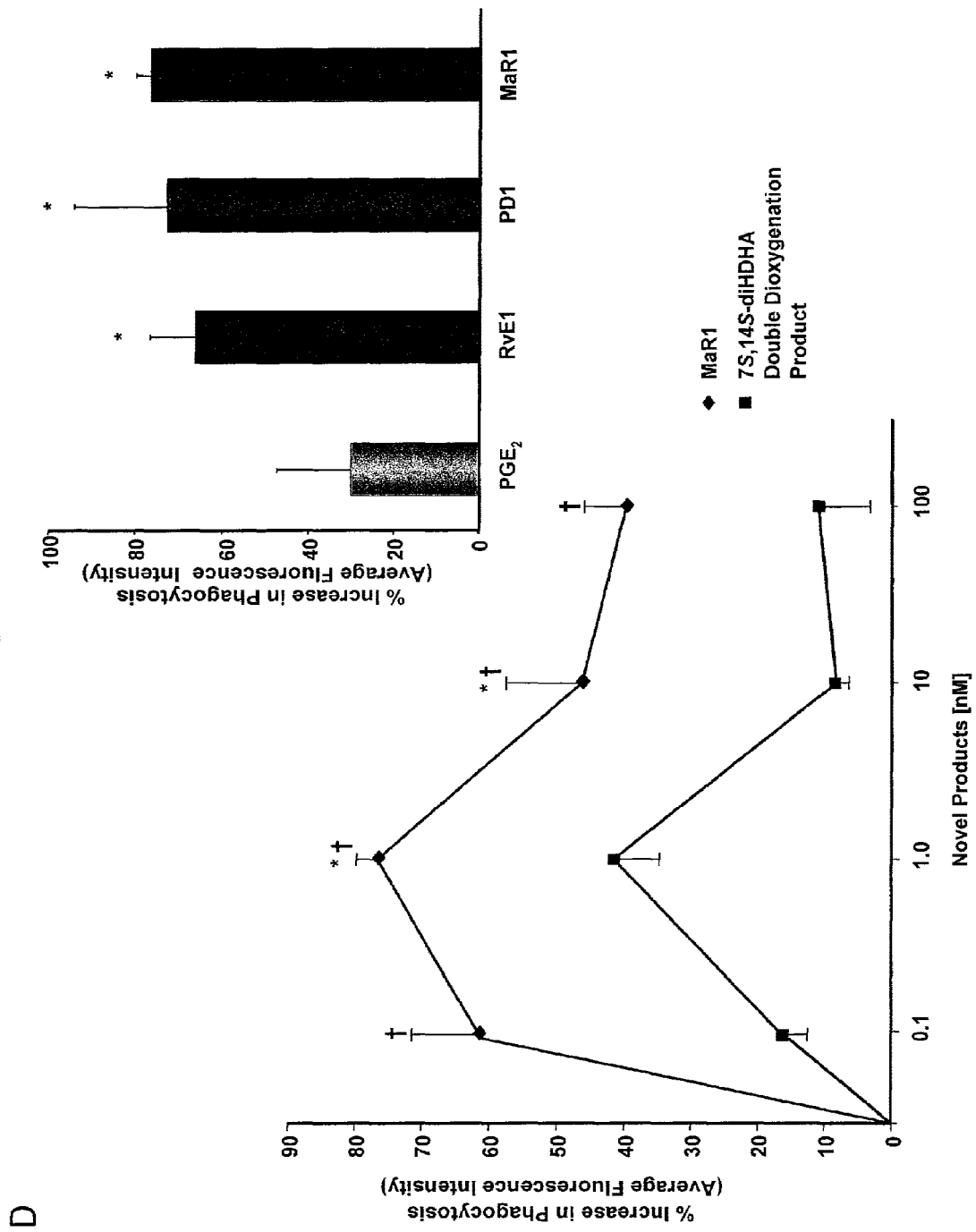
FIG. 3D. MaR1 enhances phagocytosis. MΦs (24-well plate, 10$^5$ cells/well) were exposed to indicated concentrations for 15 min followed by FITC-labeled zymosan (30 min, 37° C.). Results are mean±SEM expressed as % increase above vehicle (n=3, *, p<0.05 compared to vehicle; †, p<0.05, double dioxygenation versus MaR1). Solid diamond, MaR1. Solid box, double dioxygenation product 7S,14S-diHDHA. Inset, Comparison of MaR1 with other mediators [1 nM].

A key feature of a pro-resolving mediator, in addition to limiting PMN entry, is the dual action of stimulating MΦ uptake of apoptotic PMN and/or zymosan to stimulate resolution and microbial clearance (4, 13, 23). Next it was determined whether the new MΦ-derived compound enhanced phagocytosis and compared it to RvE1, PD1 and an eicosanoid, $PGE_2$ (FIG. 3D, inset). RvE1 and PD1 are potent enhancers of MΦ phagocytosis at concentrations as low as 1 nM (13). For direct comparison, the double dioxygenation product (7S,14S-diHDHA) was active but less potent than the new product isolated from MΦs. Thus, given its potent actions and novel structure, the MΦ product was denoted maresin 1 (MaR1).

Maresin Biosynthetic Pathway.

Figure 5:
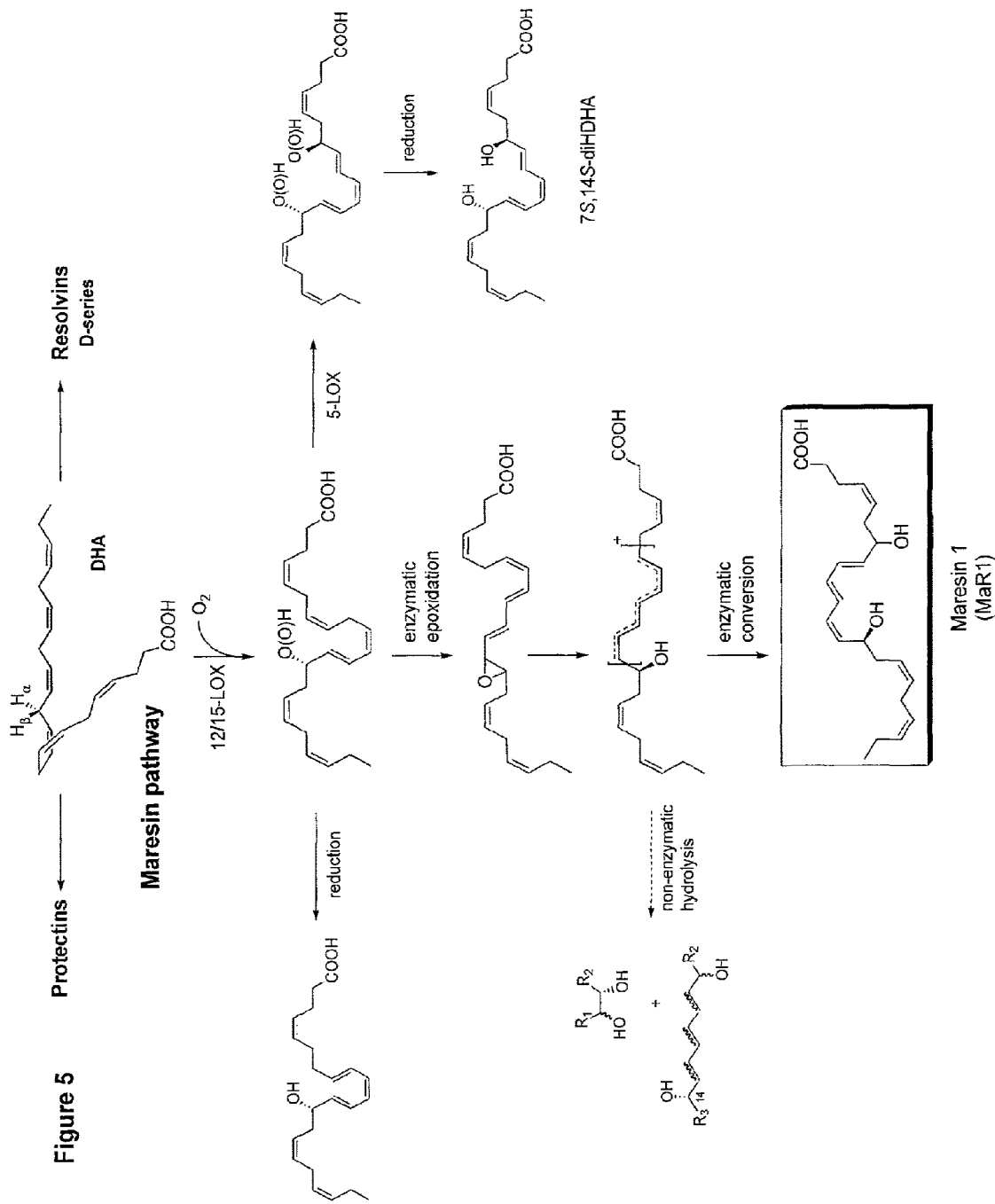
FIG. 5. Biosynthetic scheme proposed for maresin 1 and related products. Stereochemistries and double bond geometries of the new di-hydroxy containing mediators are tentative assignments and depicted in likely configurations based on biogenic synthesis, trapping and labeling.
Figure 6:
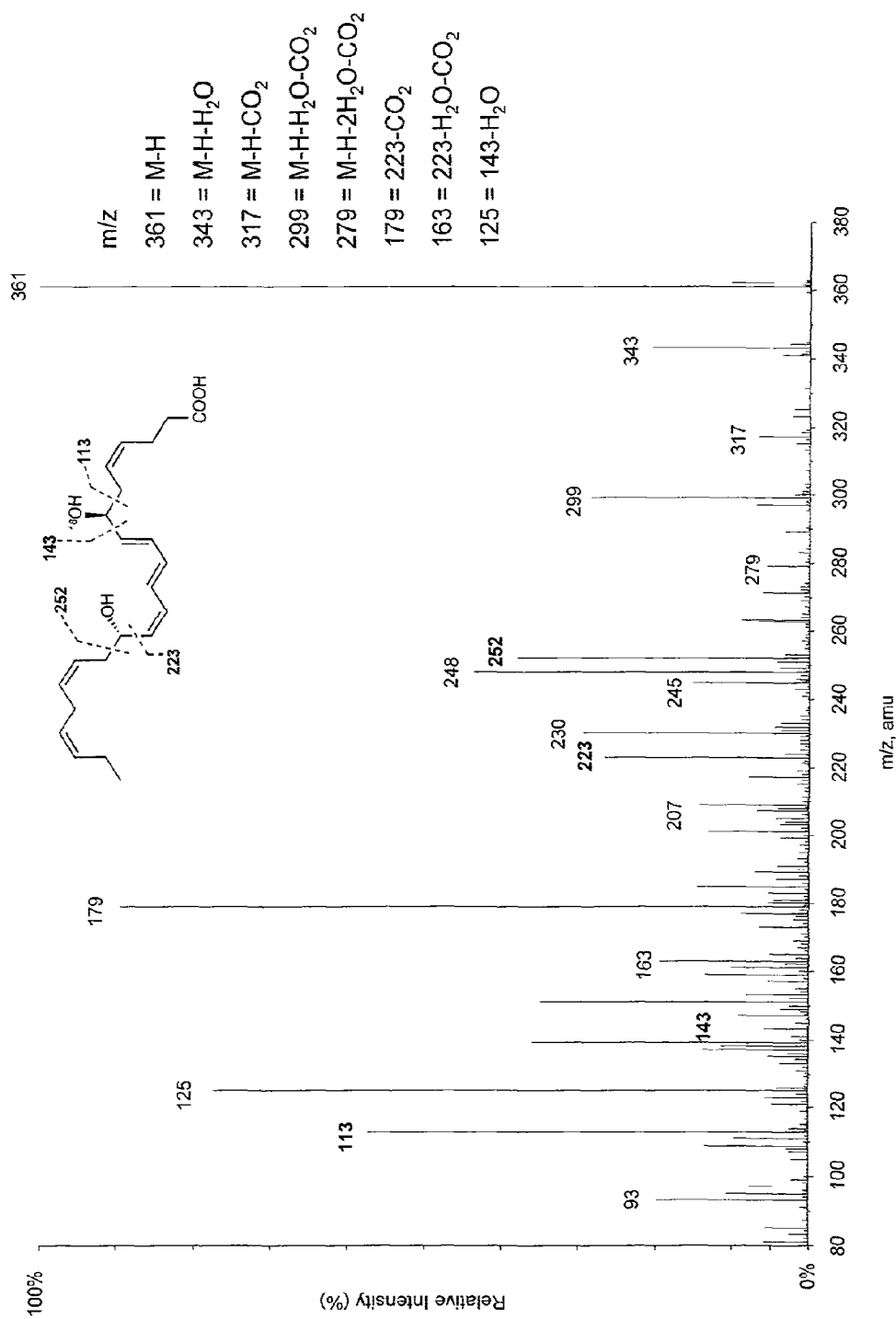
FIG. 6 shows the MS-MS spectrum of the novel product obtained with $H_2^{18}O$ and MΦ incubations.

FIG. 5 illustrates a hypothetical scheme for the maresin pathway. DHA is converted to 14-hydroperoxydocosahexaenoic acid, likely via 12-LOX in humans as shown in incubations of DHA and 12-LOX, followed by either reduction to 14S-HDHA and/or, via double dioxygenation, for example sequential 12-LOX--5-LOX, to generate 7S,14S-diHDHA. In 12/15-LOX-deficient mice, 14S-HDHA generation in peritonitis was reduced >95%. The key 14S-hydroperoxide intermediate is enzymatically converted to a 13(14)-epoxide-containing intermediate that is then enzymatically hydrolyzed via a carbonium cation to bioactive 7,14S-dihydroxydocosahexaenoic acid by creating a conjugated triene within three of the six double bonds. The results from oxygen-18 isotope incorporation using $H_2^{18}O$ demonstrated >75% of the oxygen at carbon 7 position was derived from $H_2O$ (see FIG. 6) and not from molecular oxygen, as would have been the case if this 7 position alcohol group were generated by double lipoxygenation mechanism (cf.

Figure 4:
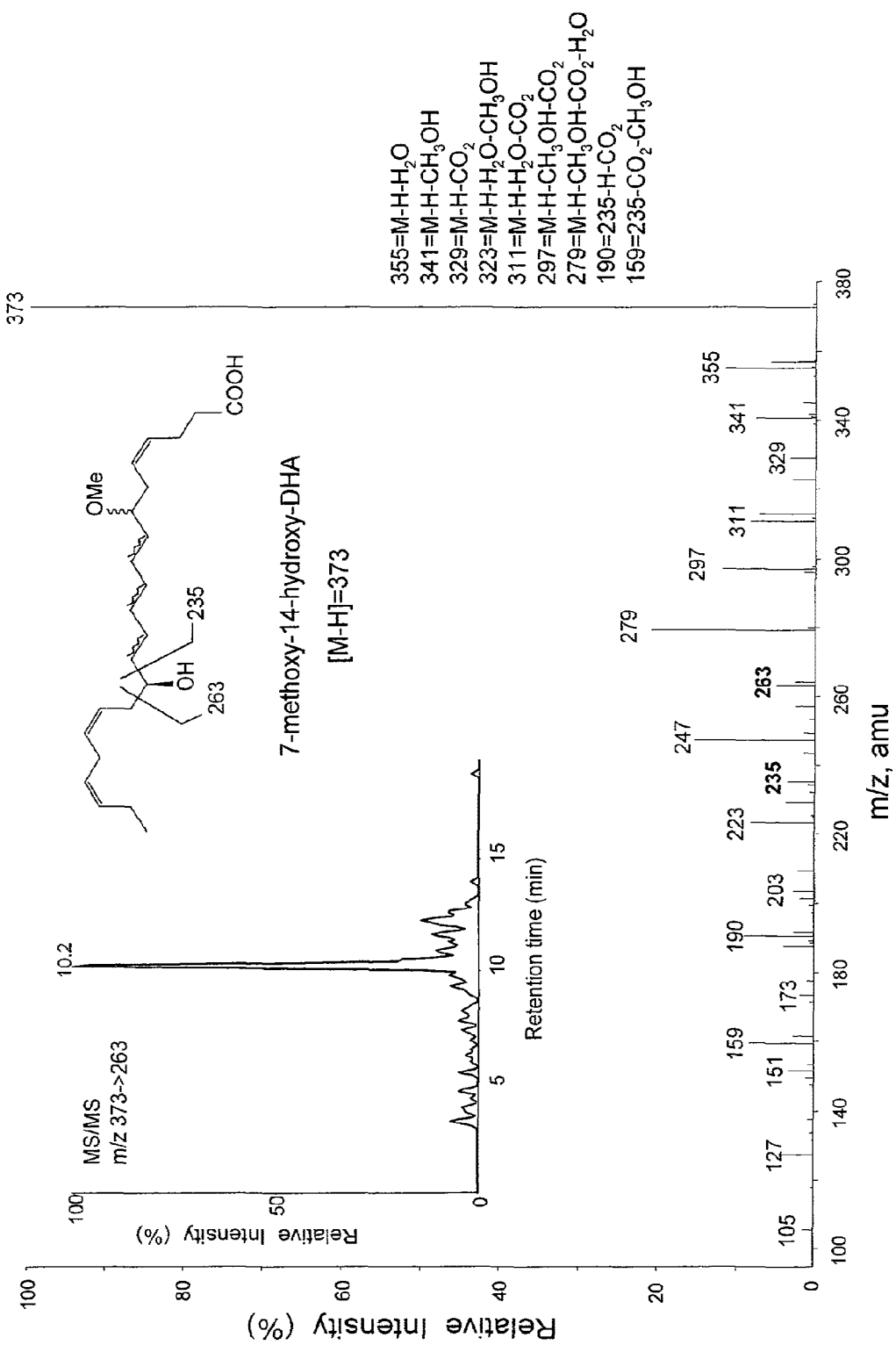
FIG. 4. Identification of methoxy trapping product from MΦs. MS/MS spectrum of m/z 373 product at 10.2 min. Inset: Extracted ion chromatogram of m/z 373-263 and deduced structure.

20). In parallel, alcohol trapping with excess acidic methanol was carried out with isolated MΦs that gave methoxy-trapping product 7-methoxy-14-hydroxydocosa-4Z,8,10,12,16Z,19Z-hexaenoic acid identified using LC/MS/MS targeted profiling. Its $MS^2$ spectrum showed ions consistent with acid-assisted attack at carbon-7 position and addition of the methoxy, giving the $MS^2$ spectrum of m/z 373 at 10.2 min (FIG. 4 inset for ion assignments, and FIG. 5). It is also possible that a methoxy addition could have occurred at carbon 13 position that could give essentially the same ions in $MS^2$. It is more likely that methoxy addition was at carbon 7, because it is the least sterically hindered end of the conjugated carbonium cation.

To provide further confirmation of the maresin pathway and biosynthetic scheme, isolated murine MΦs ($15.5 \times 10^6$ cells/3 ml, 37° C., 30 min) were incubated with zymosan and deuterium-labeled DHA-$d_5$ (10 µM) containing five deuterium atoms at 21, 21, 22, 22, and 22-carbon positions. MΦs converted DHA-$d_5$ to 14S-HDHA-$d_5$, with diagnostic ions in its mass spectrum at m/z 348, 330, 304, 286, and 205, as well as further evidence for the 7,14S-dihydroxy-containing product. The dihydroxy structure carried $d_5$, from precursor, and was confirmed with ions at m/z 364, 346, 320, and 302, and the hydroxy groups' 7- and 14-positions supported by m/z 251, 223 and 250, 221 respectively (not shown). Together these results provide support for the biosynthesis of a 13(14) epoxide intermediate by MΦs from 14S-hydroperoxydocosa-4Z,7Z,10Z,12E,16Z,19Z-hexaenoic acid (14S-HpDHA) that is enzymatically converted to the potent bioactive 7,14-dihydroxydocosa-4Z,8,10,12,16Z,19Z-hexaenoic acid MaR1 in FIG. 5.

DHA (C22:6) is an essential fatty acid and member of the n-3 family of fatty acids, which are in high levels in marine oils. It is essential for mammalian systems in that it is not biosynthesized de novo and therefore a nutritional requirement (10, 11, 21). A novel pathway herein is provided such that during resolution DHA is converted to new, potent bioactive products. This new pathway was identified using targeted mediator lipidomics of exudates from murine peritonitis and was demonstrated with both murine and human MΦs. Parallel biofunction and spectral analyses confirmed the new structures as 7,14-dihydroxy-containing products biosynthesized from DHA. One of the novel products characterized, maresin 1, proved to be a potent mediator, stopping PMN infiltration and stimulating MΦ phagocytosis. An isomer of maresin 1, 7S,14S-diHDHA, was less potent, indicating stereoselective actions in vitro and in vivo. These anti-inflammatory and pro-resolving actions were evident in nanogram range both in vitro and in vivo, suggesting that this new mediator pathway could play a key role in regulating catabasis or the return of tissues from the inflammatory state to homeostasis (8, 13).

The new compounds isolated from MΦs showed distinct and separate actions on PMN compared to mononuclear cells, as those recently identified for multifunctional mediators. Specifically, to expedite resolution, members of this new genus of endogenous mediators carry multi-level actions limiting further PMN accumulation at tissue sites and stimulate clearance by enhancing MΦ non-phlogistic phagocytosis (4, 23). This type of selectivity places a spatial and temporal as well as a functional separation between these new mediators from, for example, leukotrienes, which stimulate proinflammatory responses.

When compared to RvE1 derived from EPA and PD1/NPD1 from DHA that carries alcohol groups at carbon 10 and 17 (6, 7, 20, 21), MaR1 proved to be of comparable potency (FIG. 3). In contrast, $PGE_2$ did not enhance phagocytosis, a finding consistent with $PGE_2$ and $PGD_2$ specifically reducing MΦ phagocytosis of apoptotic cells (24). Although D-series and E-series resolvins as well as PD1 share pro-resolving and anti-inflammatory actions for the genus, each member acts at specific receptors (4, 14) and thus, given the stereospecific actions of the new pathway mediators, it is likely that they act on their own receptors separate from those for Rvs. These findings with novel chemical mediators suggest that enhancing MΦ capacity to remove apoptotic and necrotic cells at sites of inflammation and enhancing microbial particle containment along with down-regulating new PMN entry to the site may not only shorten the resolution interval (8, 13) but can also protect tissues from unwanted tissue injury damage and oxidative stress that can accompany inflammation and infection.

Figure 7:
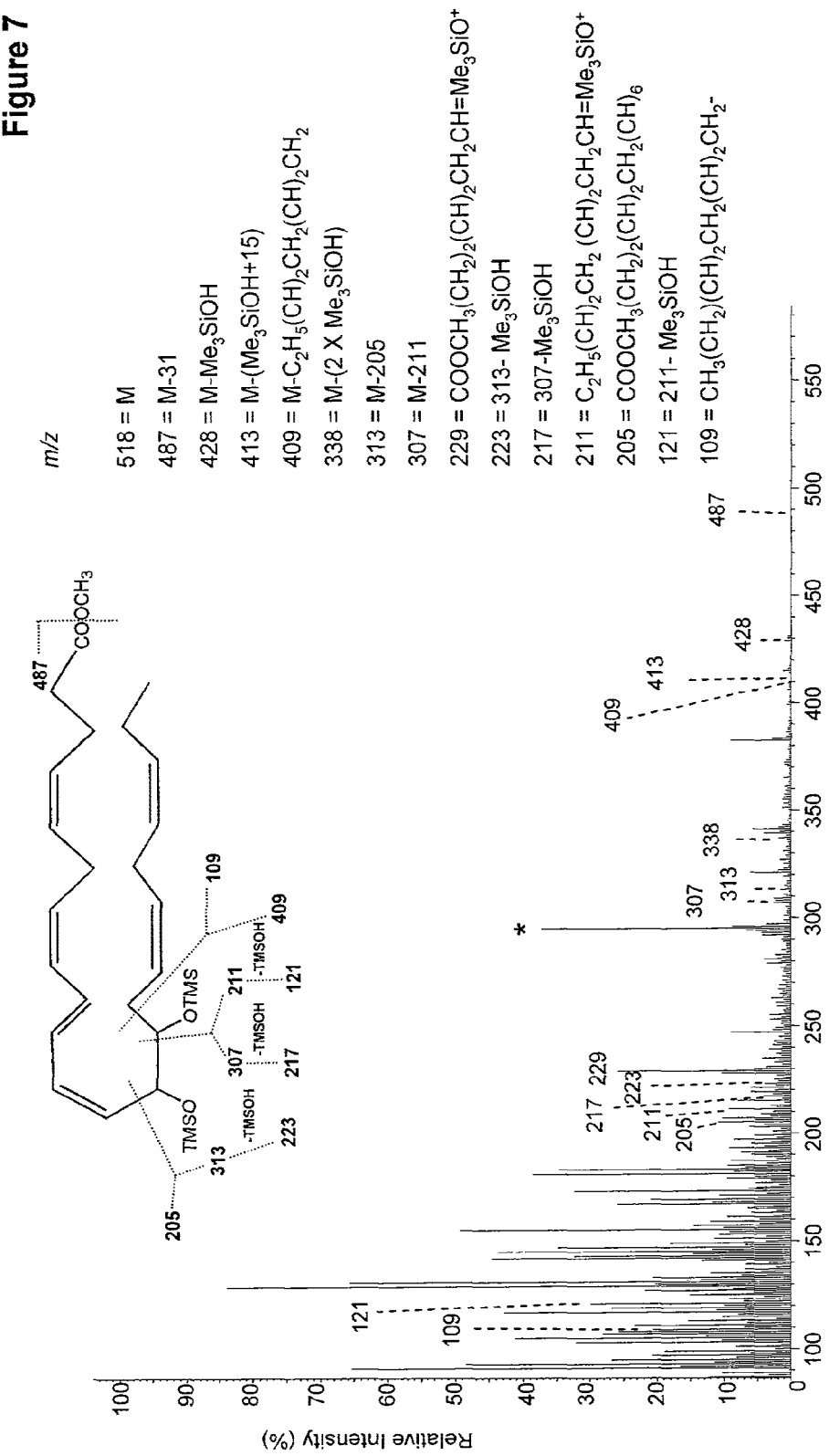
FIG. 7 is the GC-MS spectrum obtained for the 13,14-dihydroxy vicinal diol from DHA and MΦs. This product derivative was obtained after treatment with diazomethane and BSTFA to give the methyl ester, OTMS derivative.

It was also determined that the epoxide intermediate can undergo non-enzymatic hydrolysis to give 7R/S,14S-dihydroxy-containing products (that appear to coelute in this LC system) and corresponding vicinal diol, namely 13,14-dihydroxydocosahexaenoic acid (which was isolated and identified: see FIG. 5, FIG. 10 and FIG. 7). The proposed biosynthetic sequence is also supported by results from $^{18}O$ incorporation and deuterium ($d_5$)-labeled tracking from $d_5$-DHA to $d_5$-labeled maresin pathway products. Together, these results provide evidence for a highly efficient pathway in isolated resident MΦs for the biosynthesis of potent new chemical mediators via 14-lipoxygenation of DHA and subsequent enzymatic steps (FIG. 5). 4,14-di-HDHA (FIG. 10) was also identified, as a likely product of 5-LOX and 12-LOX interactions, as well as two other new products from DHA generated by MΦs, a 13(14)-epoxy-alcohol-containing docosanoid and 4S,13,14-trihydroxydocosa-5,7,9,11,16Z,19Z-hexaenoic acid.

The 14S-HDHA via arachidonate 12-LOX was first identified in gills of fish (25) and in human platelets (26), neural systems (27), and many other mammalian and invertebrate marine organisms (28). Thus, although 14S-HDHA was identified in many systems, it remained to be determined that it can serve as a marker of DHA conversion to novel bioactive mediators. It should be noted that, in addition to 14S-HDHA production by cells with 12-LOX, human 15-LOX can also contribute to this 14-LOX pathway because MΦs and other human cells possess a prominent 12-LOX and 15-LOX (2, 10, 18), and 14S-HDHA was essentially absent in 12/15-LOX-deficient mice. Given the importance of platelet 12-LOX in transcellular biosynthesis of lipid mediators (4), it is likely that cell-cell interactions can also contribute to biosynthesis of maresins and related products.

Although marine n-3 fatty acids supplements are in wide use in animals and humans because they are believed to possess therapeutic actions, convincing evidence from clinical trials supporting their actions in treating inflammatory disorders and reducing cancer risk are not without criticism (29-31). Possible sources of variation in their actions in clinical studies are a) the very high doses used (milligram to gram doses), b) absence of appropriate biomarkers of ω-3 fatty acid utilization and c) specific mediator functions evoked in pico- to nanogram range. Thus the new pathways and bioactive maresins documented here, along with resolvins, protectins and related functional metabolome, might provide a new means to mark the impact of essential ω-3 fatty acids in health and disease as well as give new therapeutic approaches.

Materials and Methods

DHA, 12-LOX (porcine), 5-LOX (human), 17-HDHA-$d_5$, and $PGE_2$-$d_4$ were purchased from Cayman Chemicals (Ann Arbor, Mich.). Zymosan A was from Sigma (St. Louis, Mo.). Solid-phase extraction materials, LC/MS/MS, and GC-MS solvents and reagents were obtained (32). Synthetic RvE1 and PD1 were prepared by total organic synthesis according to published matching criteria (32) from the NIH Specialized Research Center P50-DE016191 (to C.N.S.; Nicos A. Petasis, USC).

14S-HpDHA was prepared from DHA (~150 μM) and incubated with 5.4 U/ml isolated 12-LOX (porcine) (0.05 M phosphate buffer, 0.02% Tween 20, pH 7.4). 14S-HpDHA was isolated via RP-HPLC (Agilent 1100 Series) using a C18 column (Beckman 250 mm×10 mm×5 μm) and a mobile phase consisting of methanol/water (80/20; v/v) at 4 ml/min for 20 min and was >98% (5) configuration. Reduction with $NaBH_4$ yielded 14S-HDHA used for mass spec standard. Biogenic synthesis of the double dioxygenation product (7S,14S-diHDHA) was performed with 5-LOX enzyme incubated with 14S-HDHA. The 7S,14S-di-HDHA was scaled up for direct comparison of biological and physical properties with other novel compounds isolated from MΦs.

Macrophage Incubations.

Resident peritoneal MΦs were collected by lavage from naive mice (20-25 g, 6-8 week-old FVB mice; Charles River Labs, Wilmington, Mass.) with unlimited access to rodent diet 5001 (Lab Diet, St. Louis, Mo.) containing EPA 1.5% and DHA 1.9% of total fatty acids (19). All animal studies were approved and performed in accordance with guidelines provided by the Harvard Medical Standing Committee on Animals (Protocol Number 02570).

After centrifugation (2000 rpm) and addition of $DPBS^{+/+}$, MΦs ($15.5 \times 10^6$ cells/3 ml) were incubated with Zymosan A and 10 μM DHA or 14S-HpDHA (pH 7.45, 37° C. for 30 min). For assessing $^{18}O$ incorporation, 0.45 ml of $H_2^{18}O$ (Cambridge Isotopes, Andover, Mass.) was added to 50 μl 10×$DPBS^{+/+}$, mixed and adjusted to pH 7.3 with 1 N HCl. Isolated peritoneal MΦs ($5 \times 10^6$ cells) were suspended in $H_2^{18}O$-containing buffer. Following rapid freeze-thaw in liquid nitrogen, purified 14S-HpDHA (5 μM) was added with $A_{23187}$ (2.5 μM) for 30 min, 37° C. For alcohol trapping, isolated MΦs ($5.0 \times 10^6$ cells/100 μl) were incubated (37° C., 5 min) with 14S-HpDHA (100 μM) and $A_{23187}$ (5 μM), and incubations were stopped with 10× vol of cold methanol, apparent pH adjusted to ~pH 3 (20). All other incubations were stopped with 2 vol of cold methanol and held at −80° C. before extraction.

Mediator Lipidomics:

Product Isolation and Extractions.

Deuterated internal standard (17-HDHA-$d_5$, $PGE_2$-$d_4$; ~3 ng) was added to each incubation after protein precipitation >30 min. Samples were extracted (32) and methyl formate fractions taken for LC/MS/MS-based mediator lipidomics. UV spectra were recorded in methanol using an Agilent 4682 for quantitation and assessment of structural integrity of known mediators using appropriate extinction coefficients (32).

LC/MS/MS-based analysis was performed with an Agilent 1100 series HPLC with an ABI Sciex Instruments 3200 Qtrap linear ion trap quadrupole mass spectrometer equipped with an Agilent Eclipse Plus C18 column (4.6 mm×50 mm×1.8 μm). The instrument was run in negative ionization mode, and for enhanced product ion mode (EPI) the mobile phase consisted of methanol/water/acetic acid (60/40/0.01; v/v/v) and ramped to 80/20/0.1 (v/v/v) over 7.5 min and to 95/5/0.01 (v/v/v) in the next 4.5 min at flow rate of 400 μl/min. The flow rate was decreased to 200 μl/min for 3 min, then returned to 400 μl/min and the mobile phase was ramped up over the next 6 min to 100/0/0.01 (v/v/v). For multiple reaction monitoring (MRM) data acquisition, the mobile phase was methanol/water/acetic acid (60/40/0.01; v/v/v) ramped to 80/20/0.01 (v/v/v) after 5 min, 95/5/0.01 (v/v/v) after 8 min, and 100/0/0.01 after 14 min to wash the column.

The novel di-hydroxy containing products from DHA were monitored in enhanced product ion mode (EPI, 359.2). Ion pairs from reported MRM methods were used for profiling and quantitation of 17-HDHA, 14S-HDHA, and internal standards. Ion pair 359.2/250.2 was used to identify 7,14-dihydroxy-containing products. Criteria for matching retention time and diagnostic ions to those of synthetic references were used for identification (32). Quantitation was carried out using calibration curves constructed for each compound and recoveries were monitored using added deuterated internal standards.

Murine Peritonitis and Phagocytosis.

The 7,14-dihydroxy-containing products were isolated from methyl formate fractions obtained from murine MΦs via RP-HPLC (Agilent 1100 series) using a Beckman C18 column (250 mm×10 mm×5 μm) and methanol/water (65/35; v/v) ramped to 85/15 (v/v) for 30 min. Their actions were assessed in murine zymosan A-induced peritonitis (19). Peritonitis was initiated by intraperitoneal (i.p.) administration of 1 mg zymosan A in 1 ml of sterile saline, and each compound was administered i.v. 5 min before zymosan. At 2 h, mice were sacrificed, and peritoneal exudates harvested (5 ml $DPBS^{−/−}$ without calcium and magnesium), identified and enumerated by light microscopy and FACS. Resident MΦs were identified by FACS (8). To assess pro-resolving actions, peritoneal MΦs (24-well plate, $10^5$ cells/well) from nave mice were incubated with each compound (15 min, pH 7.45) followed by addition of FITC-labeled Zymosan A (30 min, 37° C.). Trypan blue was used to quench extracellular zymosan particles (1 min, 37° C.) followed by $DPBS^{+/+}$ (pH 7.45), and phagocytosis quantified using a Perkin-Elmer Victor$^3$.

Human Macrophage Incubations.

Human peripheral blood monocytes were isolated from healthy donors by positive selection using CD14 microbeads and a MACS column (Miltenyi Biotec). After isolation, the cells were plated in 10% FBS RPMI in the presence of GM-CSF (10 ng/ml) for 7 days to allow for differentiation to mature macrophages. Macrophages were then incubated with 14-HpDHA (5 μg) or DHA (5 μg) in the presence of zymosan (100 μg) for 30 min at 37° C. in $DPBS^{+/+}$. Incubations were terminated by the addition of 2 vol cold methanol and the samples were taken for solid phase extraction.

GC-MS Analysis.

GC-MS analysis was performed with an Agilent HP 6890 equipped with HP5973 Mass Selective Detector. Individual trimethylsilyl derivatives were prepared after the isolated compounds were treated with diazomethane. The ionization voltage was 70 eV and the ion source temperature was 230° C. An HP-5MS capillary column (30 m×0.25 mm×0.25 μm, Agilent Technologies, Wilmington, Del.) was employed with a temperature program; the initial temperature was 150° C. for 2 min, ramped to 230° C. (8 min) and 280° C. (10 min), and maintained at 280° C. for 10 min with a helium flow rate of 1.0 ml/min.

Chiral HPLC-MS/MS Analysis.

Chiralpak AD-RH (150×2×5 μm, Chiral Technologies, Inc., West Chester, Pa.) was connected to a Qtrap 3200 (Applied Biosystems), pumped by an Agilent 1100 HPLC system. Mobile phase of acetonitrile:water:acetic acid (70:

30:0.01 v/v/v) was eluted at a flow rate of 200 µl/min for 7 minutes, followed by a gradient to 100:0:0.01 (v/v/v), which was applied for the next 5 minutes.

Statistical Analysis.

All results are expressed as the mean±SEM. Statistical significance was determined using a two-tailed Student's T-test.

Synthetic Preparations of Analogs

Figure 8:
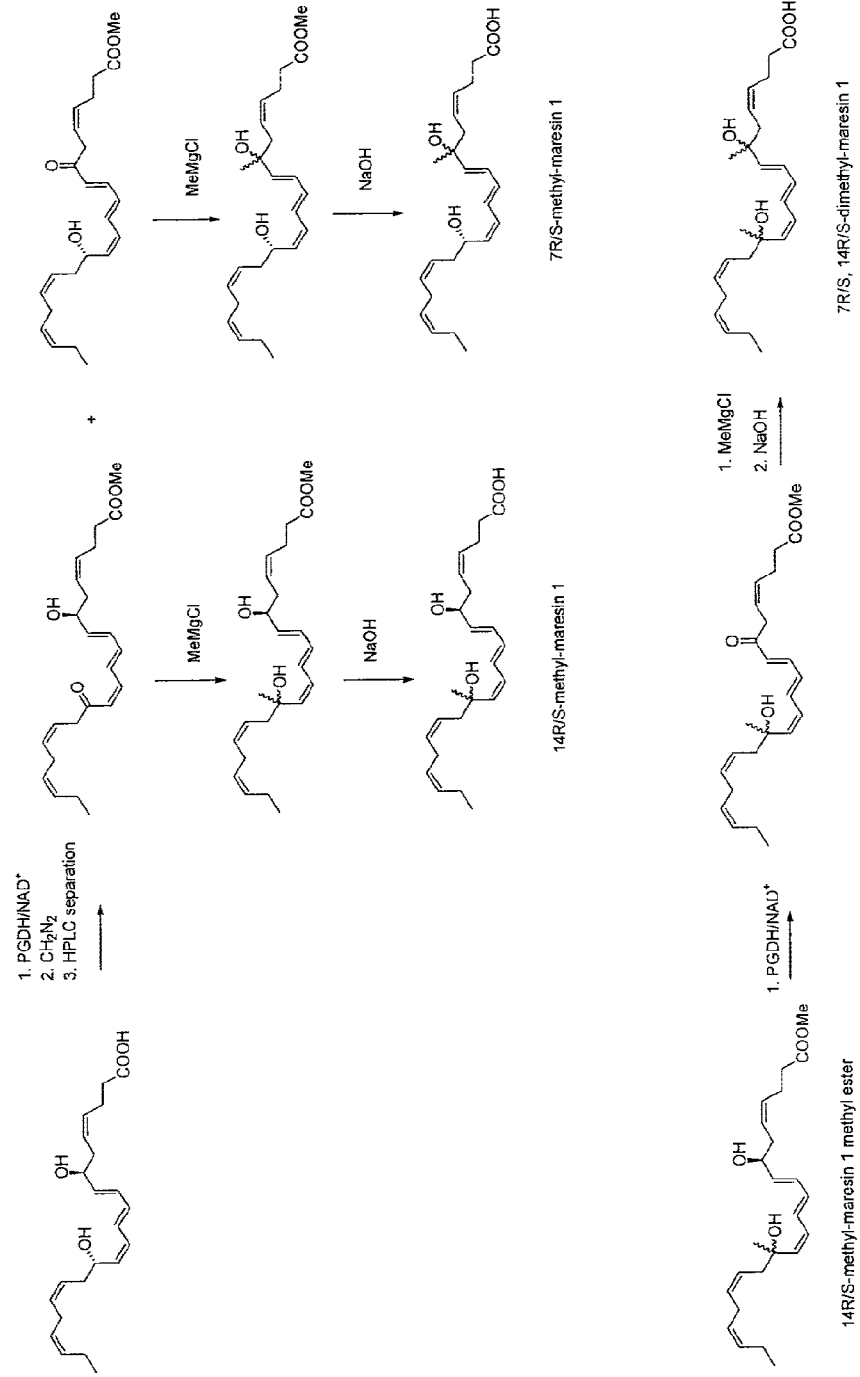
FIG. 8 is a general synthetic scheme to prepare one type of analog that is applicable to di and tri hydroxy analogs.
Figure 9:
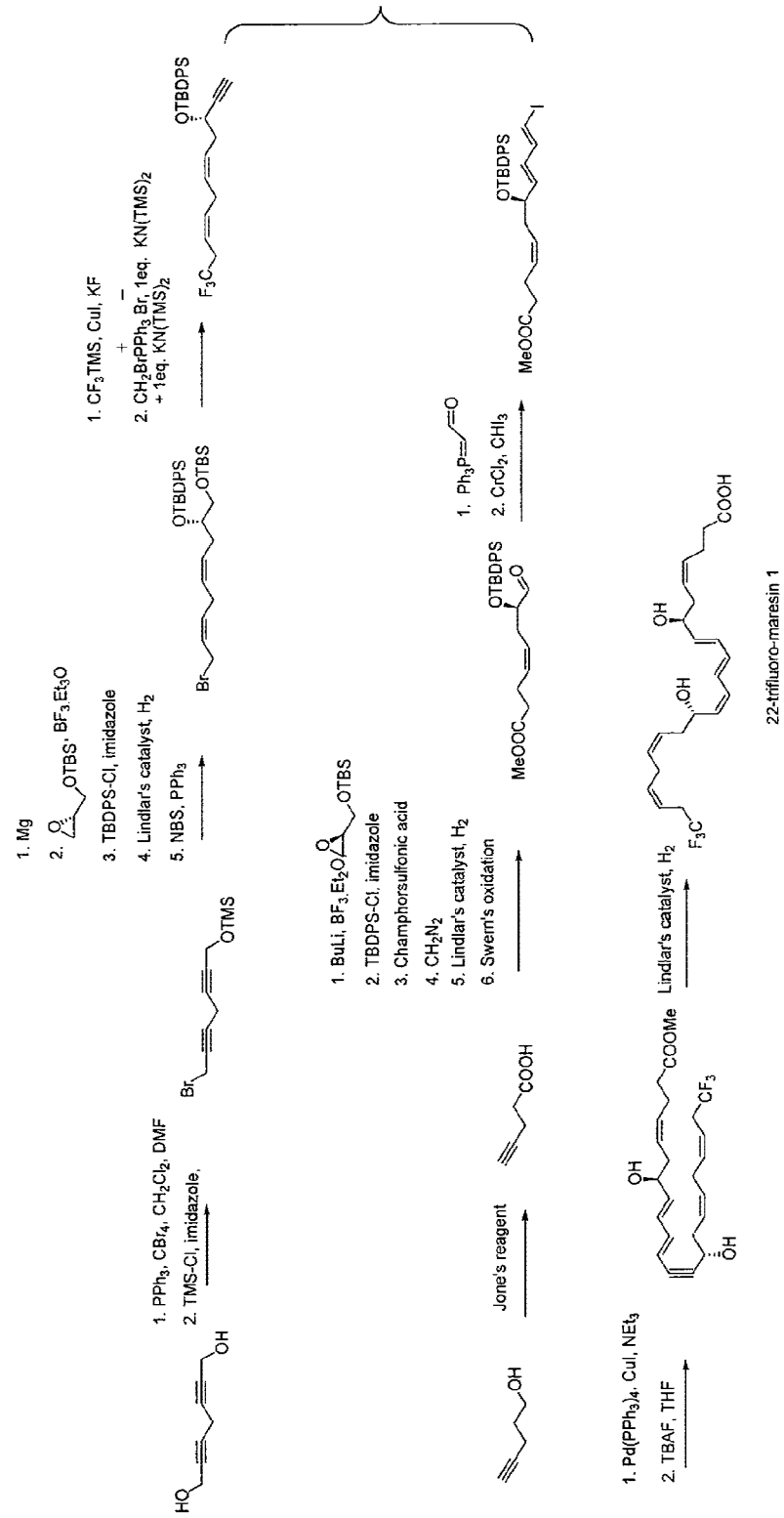
FIG. 9 is a general synthetic scheme to prepare a terminal fluorinated analog.

Not to be meant as limiting, FIGS. 8 and 9 provide synthetic methods to prepare various analogs described herein. The intermediates and products can be purified, or isolated, by methods known in the art such as by recrystallization, distillation, column chromatography, etc.

Referring to FIG. 8, a di or tri hydroxy analog can be subjected to oxidative conditions and esterified to provide ketone functionality within the alkyl chain. Functionalization with a suitable alkylating agent, such as a Grignard reagent, provides an alkylated product(s), depending on the number of ketones present and the relative amount of alkylating agent provided. The ester can be de-esterified to provide a carboxylic acid.

FIG. 9 provides a synthetic scheme to prepare trifluoromethyl terminated maresin analogs. Coupling of the trifluoromethyl hydroxy protected alkyne with an iodinated triene provides a trifluoromethyl terminated pentadiene/alkyne after deprotection of the hydroxyl groups. The intermediate can be oxidized at this stage, as described above to provide mono or diketone intermediates that can be alkylated to provide tertiary hydroxyl functionalit(ies). Alternatively, the trifluoromethyl terminated pentadiene/alkyne can be deprotected and subjected to reducing conditions to provide 22-trifluoro-maresin 1 which can be further oxidized and treated under alkylation conditions as described above to provide compounds VIa through VIc for example.

REFERENCES

1. Nathan, C. 2002. Points of control in inflammation. *Nature* 420:846-852.
2. Samuelsson, B. 1983. Leukotrienes: mediators of immediate hypersensitivity reactions and inflammation. *Science* 220:568-575.
3. Gilroy, D. W., T. Lawrence, M. Perretti, and A. G. Rossi. 2004. Inflammatory resolution: new opportunities for drug discovery. *Nat. Rev. Drug Discov.* 3:401-416.
4. Serhan, C. N., N. Chiang, and T. E. Van Dyke. 2008. Resolving inflammation: dual anti-inflammatory and pro-resolution lipid mediators. *Nat. Rev. Immunol.* 8:249-261.
5. Serhan, C. N., C. B. Clish, J. Brannon, S. P. Colgan, N. Chiang, and K. Gronert. 2000. Novel functional sets of lipid-derived mediators with antiinflammatory actions generated from omega-3 fatty acids via cyclooxygenase 2-nonsteroidal antiinflammatory drugs and transcellular processing. *J. Exp. Med.* 192:1197-1204.
6. Serhan, C. N., S. Hong, K. Gronert, S. P. Colgan, P. R. Devchand, G. Mirick, and R.-L. Moussignac. 2002. Resolvins: a family of bioactive products of omega-3 fatty acid transformation circuits initiated by aspirin treatment that counter pro-inflammation signals. *J. Exp. Med.* 196:1025-1037.
7. Hong, S., K. Gronert, P. Devchand, R.-L. Moussignac, and C. N. Serhan. 2003. Novel docosatrienes and 17S-resolvins generated from docosahexaenoic acid in murine brain, human blood and glial cells: autacoids in anti-inflammation. *J. Biol. Chem.* 278:14677-14687.
8. Bannenberg, G. L., N. Chiang, A. Ariel, M. Arita, E. Tjonahen, K. H. Gotlinger, S. Hong, and C. N. Serhan. 2005. Molecular circuits of resolution: formation and actions of resolvins and protectins. *J. Immunol.* 174:4345-4355.
9. Cotran, R. S., V. Kumar, and T. Collins, editors. 1999. Robbins Pathologic Basis of Disease. W. B. Saunders Co., Philadelphia. 1425 pp.
10. Calder, P. C. 2007. Immunomodulation by omega-3 fatty acids. *Prostaglandins Leukot. Essent. Fatty Acids* 77:327-335.
11. Simopoulos, A. P. 2002. Omega-3 fatty acids in inflammation and autoimmune diseases. *J. Am. Coll. Nutr.* 21:495-505.
12. Orr, S. K., and R. P. Bazinet. 2008. The emerging role of docosahexaenoic acid in neuroinflammation. *Curr. Opin. Investig. Drugs* 9:735-743.
13. Schwab, J. M., N. Chiang, M. Arita, and C. N. Serhan. 2007. Resolvin E1 and protectin D1 activate inflammation-resolution programmes. *Nature* 447:869-874.
14. Arita, M., F. Bianchini, J. Aliberti, A. Sher, N. Chiang, S. Hong, R. Yang, N. A. Petasis, and C. N. Serhan. 2005. Stereochemical assignment, anti-inflammatory properties, and receptor for the omega-3 lipid mediator resolvin E1. *J. Exp. Med.* 201:713-722.
15. Cash, J. L., R. Hart, A. Russ, J. P. C. Dixon, W. H. Colledge, J. Doran, A. G. Hendrick, M. B. L. Carlton, and D. R. Greaves. 2008. Synthetic chemerin-derived peptides suppress inflammation through ChemR23. *J. Exp. Med.* 205:767-775.
16. Hudert, C. A., K. H. Weylandt, J. Wang, Y. Lu, S. Hong, A. Dignass, C. N. Serhan, and J. X. Kang. 2006. Transgenic mice rich in endogenous n-3 fatty acids are protected from colitis. *Proc. Natl. Acad. Sci. U.S.A.* 103:11276-11281.
17. Gronert, K., N. Maheshwari, N. Khan, I. R. Hassan, M. Dunn, and M. L. Schwartzman. 2005. A role for the mouse 12/15-lipoxygenase pathway in promoting epithelial wound healing and host defense. *J. Biol. Chem.* 280:15267-15278.
18. Merched, A., K. Ko, K. H. Gotlinger, C. N. Serhan, and L. Chan. 2008. Atherosclerosis: Evidence for impairment of resolution of vascular inflammation governed by specific lipid mediators. *FASEB J.* 22:3595-3606.
19. Winyard, P. G., and D. A. Willoughby, editors. 2003. Inflammation Protocols. Humana, Totowa, N.J. 378 pp.
20. Serhan, C. N., K. Gotlinger, S. Hong, Y. Lu, J. Siegelman, T. Baer, R. Yang, S. P. Colgan, and N. A. Petasis. 2006. Anti-inflammatory actions of neuroprotectin D1/protectin D1 and its natural stereoisomers: assignments of dihydroxy-containing docosatrienes. *J. Immunol.* 176:1848-1859.
21. Mukherjee, P. K., V. L. Marcheselli, C. N. Serhan, and N. G. Bazan. 2004. Neuroprotectin D1: a docosahexaenoic acid-derived docosatriene protects human retinal pigment epithelial cells from oxidative stress. *Proc. Natl. Acad. Sci. U.S.A.* 101:8491-8496.
22. Fox, M. A., and J. K. Whitesell. 1997. Organic Chemistry. Jones & Bartlett, Boston. 1248 pp.
23. Godson, C., S. Mitchell, K. Harvey, N. A. Petasis, N. Hogg, and H. R. Brady. 2000. Cutting edge: Lipoxins rapidly stimulate nonphlogistic phagocytosis of apoptotic neutrophils by monocyte-derived macrophages. *J. Immunol.* 164:1663-1667.
24. Rossi, A. G., J. C. McCutcheon, N. Roy, E. R. Chilvers, C. Haslett, and I. Dransfield. 1998. Regulation of macrophage phagocytosis of apoptotic cells by cAMP. *J. Immunol.* 160:3562-3568.

25. German, J. B., G. G. Bruckner, and J. E. Kinsella. 1986. Lipoxygenase in trout gill tissue acting on arachidonic, eicosapentaenoic and docosahexaenoic acids. *Biochim. Biophys. Acta* 875:12-20.
26. Lagarde, M., M. Croset, M. Guichardant, and M. Dechavanne. 1985. Role of lipoxygenase products in platelet function: relation to fatty acid modified phospholipids. *Adv. Exp. Med. Biol.* 192:327-335.
27. Kim, H. Y., J. W. Karanian, T. Shingu, and N. Salem, Jr. 1990. Stereochemical analysis of hydroxylated docosahexaenoates produced by human platelets and rat brain homogenate. *Prostaglandins* 40:473.
28. Rowley, A. F., H. Kühn, and T. Schewe, editors. 1998. Eicosanoids and Related Compounds in Plants and Animals. Portland Press, London.
29. MacLean, C. H., S. J. Newberry, W. A. Mojica, P. Khanna, A. M. Issa, M. J. Suttorp, Y. W. Lim, S. B. Traina, L. Hilton, R. Garland, and S. C. Morton. 2006. Effects of omega-3 fatty acids on cancer risk: a systematic review. *JAMA*. 295:403-415.
30. Dwyer, J. H., H. Allayee, K. M. Dwyer, J. Fan, H. Wu, R. Mar, A. J. Lusis, and M. Mehrabian. 2004. Arachidonate 5-lipoxygenase promoter genotype, dietary arachidonic acid, and atherosclerosis. *N. Engl. J. Med.* 350:29-37.
31. Colomer, R., J. M. Moreno-Nogueira, P. P. García-Luna, P. García-Peris, A. García-de-Lorenzo, A. Zarazaga, L. Quecedo, J. del Llano, L. Usán, and C. Casimiro. 2007. N-3 fatty acids, cancer and cachexia: a systematic review of the literature. *Br. J. Nutr.* 97:823-831.
32. Serhan, C. N., Y. Lu, S. Hong, and R. Yang. 2007. Mediator lipidomics: search algorithms for eicosanoids, resolvins and protectins. *Meth. Enzymol.* 432:275-317.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A pharmaceutical composition comprising a compound having the formula (II):

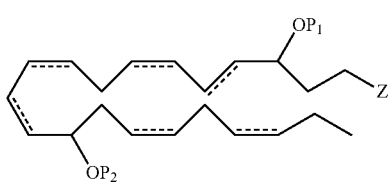

wherein each of $P_1$ and $P_2$ individually is a protecting group or a hydrogen atom;
wherein ===== is a double bond;
wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;
each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or R$^b$ groups;
each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;
each n, independently is an integer from 0 to 3; and
each R$^d$, independently is a protecting group or R$^a$;
or a pharmaceutically acceptable salt thereof; and
a pharmaceutically acceptable carrier.

2. The composition of claim 1, wherein $P_1$ and $P_2$ are both hydrogen atoms.

3. A method of treating or preventing inflammation comprising administrating to a subject in need thereof an effective amount of a compound according to claim 1.

4. A pharmaceutical composition comprising a compound having a formula (V):

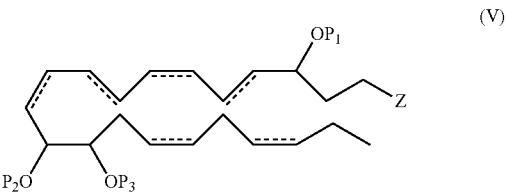

wherein each of $P_1$, $P_2$ and $P_3$ individually is a protecting group or a hydrogen atom;
wherein ===== is a double bond;
wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;
each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or $R^b$ groups;

each $R^b$ is independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2OR^d$, —S(O)$NR^cR^c$, —S(O)$_2NR^cR^c$, —OS(O)$R^d$, —OS(O)$_2R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^a$C(O)]$_nR^d$, —[NHC(O)]$_nOR^d$, —[$NR^a$C(O)]$_nOR^d$, —[NHC(O)]$_nNR^cR^c$, —[$NR^a$C(O)]$_nNR^cR^c$, —[NHC(NH)]$_nNR^cR^c$ or —[$NR^a$C($NR^a$)]$_nNR^cR^c$;

each n, independently is an integer from 0 to 3; and each $R^d$, independently is a protecting group or $R^a$;

or a pharmaceutically acceptable salt or ester thereof; and a pharmaceutically acceptable carrier.

5. The composition of claim 4, wherein $P_1$, $P_2$ and $P_3$ are all hydrogen atoms.

6. A method of treating or preventing inflammation comprising administrating to a subject in need thereof an effective amount of a compound according to claim 4.

7. A pharmaceutical composition comprising a compound of formula (IIa, IIb, or IIc):

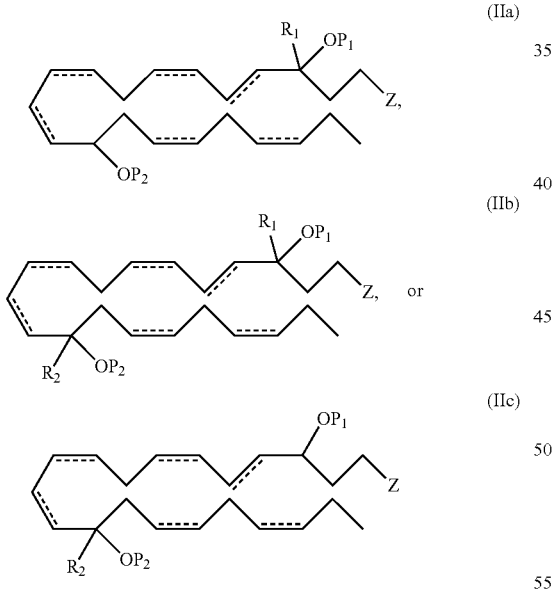

wherein each of $P_1$ and $P_2$ individually is a protecting group or a hydrogen atom;

wherein ===== is a double bond;

wherein Z is —C(O)$OR^d$, —C(O)$NR^cR^c$, —C(O)H, —C(NH)$NR^cR^c$, —C(S)H, —C(S)$OR^d$, —C(S)$NR^cR^c$, or —CN;

each $R^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each $R^c$, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or $R^b$ groups;

each $R^b$ is independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2OR^d$, —S(O)$NR^cR^c$, —S(O)$_2NR^cR^c$, —OS(O)$R^d$, —OS(O)$_2R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^a$C(O)]$_nR^d$, —[NHC(O)]$_nOR^d$, —[$NR^a$C(O)]$_nOR^d$, —[NHC(O)]$_nNR^cR^c$, —[$NR^a$C(O)]$_nNR^cR^c$, —[NHC(NH)]$_nNR^cR^c$ or —[$NR^a$C($NR^a$)]$_nNR^cR^c$;

$R_1$ and $R_2$, if present, is/are each independently selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each n, independently is an integer from 0 to 3; and each $R^d$, independently is a protecting group or $R^a$;

or a pharmaceutically acceptable salt or ester thereof; and a pharmaceutically acceptable carrier.

8. The composition of claim 7, wherein $P_1$ and $P_2$ are both hydrogen atoms.

9. A method of treating or preventing inflammation comprising administrating to a subject in need thereof an effective amount of a compound according to claim 7.

10. A pharmaceutical composition comprising a compound having the formula (Va, Vb, Vc, Vd, Ve, Vf, or Vg):

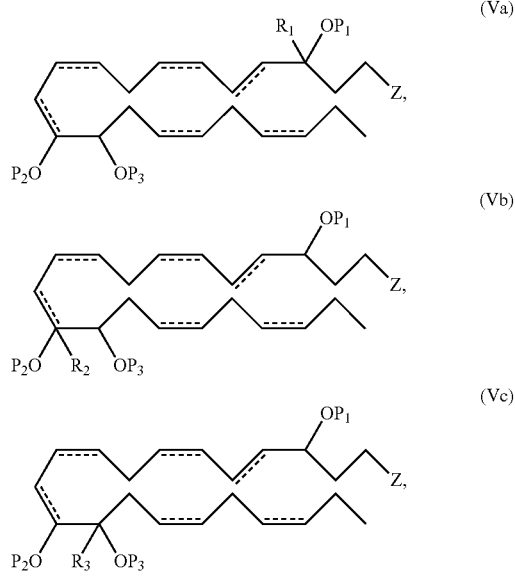

-continued

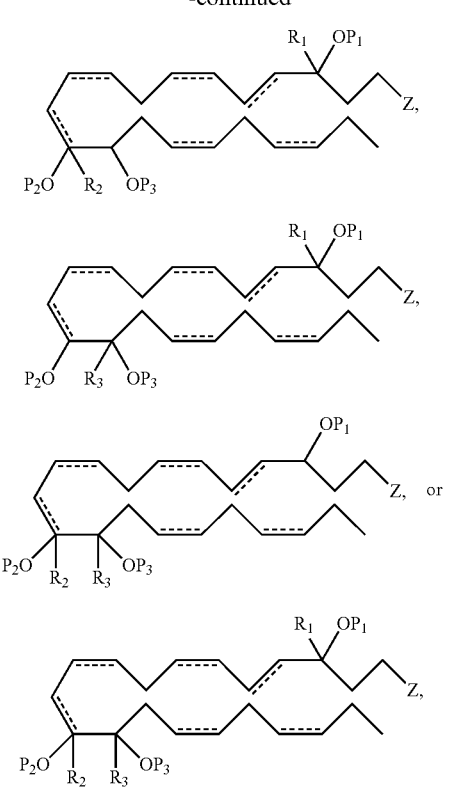

(Vd)

(Ve)

(Vf)

(Vg)

wherein each of $P_1$, $P_2$ and $P_3$ individually is a protecting group or a hydrogen atom;
wherein ===== is a double bond;
wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;
each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or R$^b$ groups;
each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;
$R_1$, $R_2$ or $R_3$, if present, is/are each independently selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each n, independently is an integer from 0 to 3; and
each R$^d$, independently is a protecting group or R$^a$;
or a pharmaceutically acceptable salt or ester thereof; and
a pharmaceutically acceptable carrier.

11. The composition of claim 10, wherein P1, P2 and P3 are all hydrogen atoms.

12. A method of treating or preventing inflammation comprising administrating to a subject in need thereof an effective amount of a compound according to claim 10.

13. A pharmaceutical composition comprising a compound having the formula (VIa, VIb or VIc):

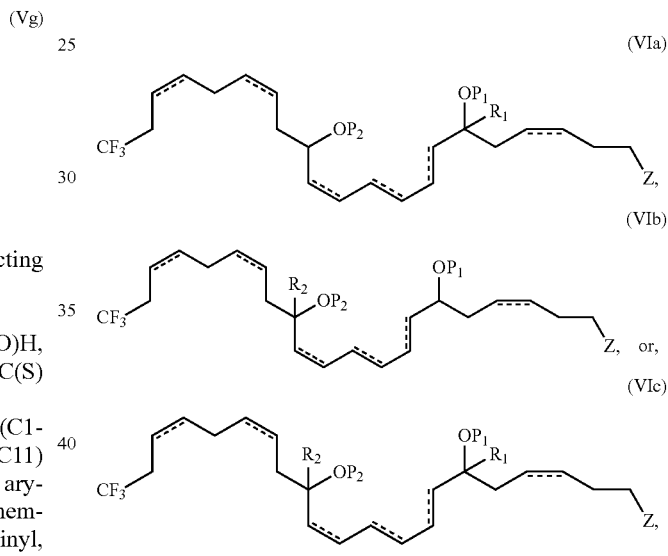

(VIa)

(VIb)

(VIc)

wherein each of $P_1$ and $P_2$ individually is a protecting group or a hydrogen atom;
wherein ===== is a double bond;
wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN;
each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or R$^b$ groups;

each $R^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^d$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

R$_1$ and R$_2$, if present, is/are each independently selected from (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each n, independently is an integer from 0 to 3; and each R$^d$, independently is a protecting group or R$^a$;

or a pharmaceutically acceptable salt or ester thereof; and a pharmaceutically acceptable carrier.

14. The composition of claim 13, wherein P$_1$ and P$_2$ are both hydrogen atoms.

15. A method of treating or preventing inflammation comprising administrating to a subject in need thereof an effective amount of a compound according to claim 13.

* * * * *

UNITED STATES PATENT AND TRADEMARK OFFICE
CERTIFICATE OF CORRECTION

PATENT NO. : 9,611,238 B2
APPLICATION NO. : 14/557151
DATED : April 4, 2017
INVENTOR(S) : Charles N. Serhan et al.

It is certified that error appears in the above-identified patent and that said Letters Patent is hereby corrected as shown below:

In the Specification

Column 6, Line 38, "$R^d$ and" should be --Rd, $R^1$ and--.

Column 15, Line 13, "C Spectra" should be --$^C$Spectra--.

Column 22, Line 35, "indene" should be --indane--. (First Occurrence)

Column 24, Line 59, "spa" should be --$sp^3$--.

Signed and Sealed this
Nineteenth Day of February, 2019

Andrei Iancu
*Director of the United States Patent and Trademark Office*

UNITED STATES PATENT AND TRADEMARK OFFICE
CERTIFICATE OF CORRECTION

PATENT NO. : 9,611,238 B2
APPLICATION NO. : 14/557151
DATED : April 4, 2017
INVENTOR(S) : Charles N. Serhan et al.

It is certified that error appears in the above-identified patent and that said Letters Patent is hereby corrected as shown below:

In the Specification

Column 1, Lines 22-25:
"The work leading to this invention was supported in part by National Institutes of Health (NIH) grants P50-DE016191 and R37-GM038765. The U.S. Government therefore may have certain rights in the invention."

Should be:
--This invention was made with government support under GM038765, and DE016191 awarded by the National Institutes of Health. The government has certain rights in the invention.--.

Signed and Sealed this
Ninth Day of May, 2023

Katherine Kelly Vidal
Director of the United States Patent and Trademark Office